(12) United States Patent
Park et al.

(10) Patent No.: US 11,866,765 B2
(45) Date of Patent: Jan. 9, 2024

(54) COMPOSITION FOR IMPROVING MOLECULAR BARCODING EFFICIENCY AND USE THEREOF

(71) Applicant: GENINUS INC., Seoul (KR)

(72) Inventors: Dong Hyun Park, Chuncheon-si (KR); Jong Suk Chung, Hwaseong-si (KR); Seung Ho Shin, Seoul (KR); Sol Yi Kim, Seongnam-si (KR); Hyeyeun Lim, Bucheon-si (KR); Hyeong Been Park, Seoul (KR)

(73) Assignee: GENINUS INC., Seoul (KR)

( * ) Notice: Subject to any disclaimer, the term of this patent is extended or adjusted under 35 U.S.C. 154(b) by 268 days.

(21) Appl. No.: 17/225,597

(22) Filed: Apr. 8, 2021

(65) Prior Publication Data

US 2022/0275425 A1    Sep. 1, 2022

(30) Foreign Application Priority Data

Feb. 26, 2021  (KR) ........................ 10-2021-0026287

(51) Int. Cl.
  *C12P 19/34*  (2006.01)
  *C12Q 1/6806*  (2018.01)
  *C12N 15/10*  (2006.01)
  *C12Q 1/6855*  (2018.01)
  *C12Q 1/6869*  (2018.01)

(52) U.S. Cl.
  CPC ....... *C12Q 1/6806* (2013.01); *C12N 15/1065* (2013.01); *C12Q 1/6855* (2013.01); *C12Q 1/6869* (2013.01)

(58) Field of Classification Search
  CPC .................................................. C12Q 1/6869
  See application file for complete search history.

(56) References Cited

U.S. PATENT DOCUMENTS

| | | | |
|---|---|---|---|
| 9,340,826 B2 | 5/2016 | Bang et al. | |
| 9,850,482 B2 | 12/2017 | Kwon et al. | |
| 2015/0284712 A1 | 10/2015 | Kurihara et al. | |
| 2018/0251848 A1* | 9/2018 | Diehn ................. | C12Q 1/6886 |
| 2019/0185932 A1 | 6/2019 | Kim et al. | |
| 2020/0123538 A1 | 4/2020 | Gole et al. | |
| 2022/0127597 A1* | 4/2022 | Chan ................... | C12Q 1/6806 |
| 2022/0177963 A1* | 6/2022 | Chen .................. | C12N 15/1093 |
| 2022/0243267 A1* | 8/2022 | Yencho ............... | C12Q 1/6874 |

FOREIGN PATENT DOCUMENTS

| | | |
|---|---|---|
| KR | 2013-0018575 A | 2/2013 |
| KR | 2014-0111224 A | 9/2014 |
| KR | 10-1575457 | 12/2015 |
| KR | 2016-0141680 A | 12/2016 |
| KR | 2017-0133270 A | 12/2017 |

OTHER PUBLICATIONS

Griffiths et al., Nature Communications 9 (2667), 1-6 (2018). (Year: 2018).*
International Search Report and Written Opinion, PCT App. No. PCT/KR2021/002492, dated Nov. 23, 2021 (9 pages).

* cited by examiner

*Primary Examiner* — Kenneth R Horlick
(74) *Attorney, Agent, or Firm* — NIXON PEABODY LLP; Jeffrey L. Costellia

(57) ABSTRACT

The present disclosure relates to a composition for improving molecular barcoding efficiency and a use thereof, and provided are a method for preparing a DNA library, a molecular barcoding method for nucleic acid sequencing, and a composition for preparing a DNA library. According to the method and composition, by using a barcode sequence arranged to include the position of a first nucleotide in an adapter on the basis of a terminal region of the adapter ligated with a DNA fragment, molecular barcoding switching can be reduced and the accuracy of nucleic acid sequencing can be improved.

11 Claims, 15 Drawing Sheets

Specification includes a Sequence Listing.

FIG. 14

/5Phos/GGAGATCGGAAGAGC ACACGTCTGAACTCCAGTCACCCGGAACGAAATCTCGTATGCCGTCTTCTGCTTG

TCCTCTAGCCCTTCTCG CAGCACATCCCTTTCTCACAGTATCACATCCACATCTAGAGCCACCAGCGGGCATAGTAA

COMPOSITION FOR IMPROVING MOLECULAR BARCODING EFFICIENCY AND USE THEREOF

CROSS-REFERENCE TO RELATED APPLICATION

This application is based on and claims priority under 35 U.S.C. § 119 to Korean Patent Application No. 10-2021-0026287, filed on Feb. 26, 2021, in the Korean Intellectual Property Office, the disclosure of which is incorporated by reference herein in its entirety.

BACKGROUND

1. Field

The present disclosure relates to a composition for improving molecular barcoding efficiency and a use thereof.

2. Description of the Related Art

Various biometric information is expressed as DNA sequence genes, and complete DNA sequence information of an individual is very important for understanding life phenomena and obtaining disease-related information. The key to deciphering DNA sequence information, that is, genome sequencing, is to identify individual differences and ethnic characteristics, identify congenital causes including chromosomal abnormalities in diseases related to genetic abnormalities, and find genetic defects in complex diseases such as diabetes and hypertension. In addition, sequencing data is very important because information such as gene expression, gene diversity, and their interactions can be widely used in molecular diagnostics and therapeutic fields.

As a method for genome sequencing, Next Generation Sequencing (NGS) has been applied since 2007, and the development of such NGS has enabled easy and low-cost analysis compared to traditional methods. Representative examples of next-generation genome sequencers that implement next-generation sequencing methods include Roche/454, Illumina/Solexa, and SOLiD from Life Technologies (ABI). These next-generation sequencing devices can read more than 80 million sequences in 7 hours. With the development of this technology, the next-generation sequencing method, which was previously used only for research due to the enormous cost of testing, can be used in medical clinical tests.

Meanwhile, owing to the development of sequencing technology, a variety of attempts have been made to discover various types of structural variations, but a significant level of false positives or false negatives are generated in the analysis process. Thus, various attempts are being made to solve such a problem. As a technology to solve the problem, for example, molecular barcoding technology is widely used, but an adapter that is not removed in the purification process after ligation acts as a primer in the PCR amplification process, causing errors in sample information, and there are still technical limitations in terms of sensitivity and specificity of detection.

Today, as the field of precision medical-based diagnosis/treatment technology begins to draw attention, the need for more precise and accurate analysis is emerging. Accordingly, research into molecular barcode technology is being actively conducted (Korea Patent Registration No. 10-1575457), which is, however, still incomplete.

SUMMARY

An aspect is to provide a method for preparing a DNA library for nucleic acid sequencing.

Another aspect is to provide a molecular barcoding method for nucleic acid sequencing.

Another aspect is to provide a composition for preparing a DNA library for nucleic acid sequencing.

Other objects and advantages of the present application will become more apparent from the following detailed description in conjunction with the appended claims. The contents that are not set forth in the specification can be sufficiently recognized and inferred by a person skilled in the art to which the present disclosure belongs or the art similar thereto, and descriptions thereof will be omitted.

Additional aspects will be set forth in part in the description which follows and, in part, will be apparent from the description, or may be learned by practice of the presented embodiments of the disclosure.

The terms used in examples of the present disclosure have been selected as general terms currently used as widely as possible in the art in consideration of acts in the present embodiments, but these terms may vary according to the intention or precedent cases of a person skilled in the art, the advent of new technologies. In addition, in certain cases, there may be an arbitrarily selected term, in which case the meaning thereof will be described in detail in the description of the corresponding embodiment. Therefore, the term used in various examples of the present specification should be defined based on the meaning of the term rather than the name of the term, and the contents of the present specification throughout the present specification.

In each description, when it is said that a part is connected to another part, this includes not only a case in which it is directly connected, but also a case in which it is organically connected with another component interposed therebetween. Also, when it is said that a part "includes" a certain component, it means that other components may be further included rather than excluding other components unless specifically stated to the contrary. As used herein, terms such as "consisting of" or "comprising" should not be construed as necessarily including all of the various components or various steps described in the specification, but should be construed that some components or some steps thereof may not be included, or may further include additional components or steps.

Each description should not be construed as limiting the scope of rights, and what can be easily inferred by a person skilled in the art should be construed as belonging to the scope of rights.

In an aspect, provided is a method for preparing a DNA library for nucleic acid sequencing, the method comprising the steps of: ligating an adapter comprising a barcode sequence to both ends of a DNA fragment extracted and fragmented from a target sample; separating the ligated DNA fragment into single strands; and amplifying the single-stranded DNA fragment ligated with the adapter through a polymerase chain reaction by using a primer that recognizes the adapter, wherein the barcode sequence has a length of 1 nt to 10 nt and is arranged to include the position of a first nucleotide in the adapter, on the basis of a terminal region of the adapter ligated with the DNA fragment.

In addition, in another aspect, provided is a molecular barcoding method for nucleic acid sequencing, comprising the step of ligating an adapter comprising a barcode sequence to both ends of a DNA fragment extracted and fragmented from a target sample, wherein the barcode sequence has a length of 1 nt to 10 nt and is arranged to include the position of a first nucleotide in the adapter, on the basis of a terminal region of the adapter ligated with the DNA fragment.

As used herein, the term "DNA library" refers to a product of DNA sample processing as a result of pretreatment for nucleic acid sequencing on a target sample. The DNA library may refer to, for example, a plurality of reads for sequence analysis, and more specifically, a plurality of reads into which a unique barcode sequence is introduced. Typically, the DNA library is prepared by ligating adapter oligonucleotides to both ends of a DNA fragment, and an amplified product thereof may also be included. The DNA library may be prepared through a series of processes including, for example, i) randomly cutting a DNA sample to obtain DNA fragments (DNA fragmentation); ii) reinforcing both ends of two single-stranded DNAs to form a blunt end structure (end repair); iii) forming an overhang structure by conjugating adenine to the 3' end of a double-stranded DNA (adenine conjugation); iv) ligating the adenine-conjugated adapter to the end of the double-stranded DNA (adapter attachment); v) separating the double-stranded DNA conjugated by the adapter into single strands by using a specific enzyme (single-stranded separation); and vi) amplifying the DNA fragment attached to an adapter sequence through a polymerase chain reaction (PCR) (PCR amplification). The DNA library may be interpreted as including not only a final product, but also an intermediate product in each of the above-mentioned steps.

Techniques known in the art may be applied to each of the above-mentioned steps in a non-limiting manner. For example, T4 DNA ligase, T7 DNA ligase, or a ligase capable of temperature cycling may be used in the adapter attachment step, or the PCR amplification process is performed 4 to 12 times, 4 to 10 times, 4 to 8 times, 4 to 6 times, 6 to 12 times, 6 to 10 times, 6 to 8 times, 8 to 12 times, 8 to 10 times, or 10 to 12 times may be performed, and other techniques widely used in the art may be used in analyzing the nucleic acid sequence according to an embodiment.

As used herein, the term "molecular barcode" refers to a nucleotide sequence unique to each DNA fragment present in a target sample, and makes it possible to distinguish DNA fragments present in the target sample from one another. According to the conventional molecular barcode technology, in the PCR amplification process, when an adapter having an erroneous barcode sequence or a unique identifier (UID) acts as a primer in a subsequent PCR reaction, an erroneous PCR copy may be generated (molecular barcode switching phenomenon), and thus, in the genome analysis process, false-positive reads may be increased and the sensitivity of positive detection may be decreased due to an increase in normal control reads, thereby reducing the reliability of genetic information analysis results with high depth Under these technical backgrounds, the present inventors confirmed that the above-mentioned conventional problems can be overcome by arranging, with respect to a terminal region of the adapter ligated with the DNA fragment, a specific nucleotide at a specific position in the barcode sequence arranged to include the position of a first nucleotide in the adapter and the terminal region, and based on this finding, the present invention was completed.

As used herein, the term "target sample" may be derived from a subject or cell. The subject may be a mammal, including humans, cattle, horses, pigs, sheep, goats, dogs, cats, and rodents. The cell may be a cell or cell line derived from a subject. In addition, the target sample may be a biological sample. The biological sample may be obtained from, for example, blood, plasma, serum, urine, saliva, mucous membrane, secretion, sputum, feces, tears, or a combination thereof. The biological sample may be a sample of eukaryotic cells, prokaryotic cells, viruses, bacteriophages, etc. derived from various species.

As used herein, the term "nucleic acid sequencing analysis" may be next generation sequencing (NGS). The nucleic acid sequencing may be used interchangeably with nucleotide sequence analysis, sequence analysis, or sequencing. The NGS may be used interchangeably with massive parallel sequencing or second-generation sequencing. The NGS, which is a technique for simultaneous sequencing of nucleic acids of a large number of fragments, may fragment whole genomes in a chip-based and polymerase chain reaction (PCR)-based paired end format and then perform sequencing on the fragments at a very high speed by hybridization. The NGS may be performed by, for example, 454 platform (Roche), GS FLX titanium, Illumina MiSeq, Illumina HiSeq, Illumina HiSeq 2500, Illumina Genome Analyzer, Solexa platform, SOLiD System (Applied Biosystems), Ion Proton (Life Technologies), Complete Genomics , Helicos Biosciences Heliscope, Pacific Biosciences single molecule real-time (SMRT™) technology, or a combination thereof. The nucleic acid sequencing may be a nucleic acid sequencing method for analyzing only a region of interest. The nucleic acid sequencing may include, for example, NGS-based targeted sequencing, targeted deep sequencing, or panel sequencing. Here, the nucleic acid may be a genome or a fragment thereof. As used herein, the term "genome" is a generic term for the whole of chromosomes, chromatin, or genes. The genome or fragment thereof may be isolated DNA. A method for extracting or isolating the nucleic acid from the cell may be performed by a method known to those skilled in the art. Here, fragmentation refers to physically, chemically, or enzymatically cleaving a genome, and through the above process, reads having various lengths may be generated. As used herein, the term "read" refers to sequence information of one or more nucleic acid fragments generated in nucleic acid sequencing, wherein the read is about 10 bp to about 2000 bp, for example, about 15 bp to about 1500 bp, about 20 bp to about 1000 bp, about 20 bp to about 500 bp, about 20 bp to about 200 bp, about 20 bp to about 100 bp, but is not limited thereto.

In the step of ligating the adapter comprising the barcode sequence, the barcode sequence may have a length of 1 nt to 10 nt, and may be arranged to include the position of a first nucleotide in the adapter, on the basis of the terminal region of the adapter ligated with the DNA fragment.

As used herein, the term "adapter" refers to an oligonucleotide including a barcode sequence for discriminating a plurality of DNA fragments, and may be of a Y-shaped (Forked) or U-shaped (Hairpin) form. For example, the adapter may be cut from the U-shaped adapter to have a Y-shaped end by using an enzyme such as uracil-specific excision reagent (USER), but is not limited thereto.

In addition, the 3' end of the double-stranded DNA fragment has an overhang structure by adenine conjugation, and for ligation with the DNA fragment, the adapter may consist of a double strand, and thymine may be conjugated to the 3' end of the adapter. Here, the length of the adapter sequence may be 40 nt to 100 nt, 40 nt to 90 nt, 40 nt to 80 nt, 40 nt to 70 nt, 40 nt to 60 nt, 40 nt to 50 nt, 50 nt to 100 nt, 50 nt to 90 nt, 50 nt to 80 nt, 50 nt to 70 nt, 50 nt to 60 nt, 60 nt to 100 nt, 60 nt to 90 nt, 60 nt to 80 nt, 60 nt to 70 nt, 70 nt to 100 nt, 70 nt to 90 nt, 70 nt to 80 nt, 80 nt to 100 nt, or 80 nt to 90 nt, but is not limited thereto.

The adapter may be, for example, a Y-shaped double strand including a complementary bond in a partial region, as shown in FIG. 14, and may have a barcode sequence located at the end of a region where the complementary bond is formed, in a single-stranded oligonucleotide constituting the adapter.

As used herein, the term "barcode" may be used interchangeably with "index" or "unique identifier (UID)", and refers to an oligonucleotide of 1 nt 10 nt in length. The barcode sequence is included in the adapter, and thus may refer to a pair or a combination that forms a complementary bond. Here, the length of the barcode sequence may be 1 nt to 10 nt, 1 nt to 8 nt, 1 nt to 6 nt, 1 nt to 4 nt, 1 nt to 2 nt, 3 nt to 10 nt, 3 nt to 8 nt, 3 nt to 6 nt, 1 nt to 4 nt, 5 nt to 10 nt, 5 nt to 8 nt, 5 nt to 6 nt, 7 nt to 10 nt, or 7 nt to 8 nt, but is not limited thereto.

In a specific embodiment, the barcode sequence may be arranged to include the position of a first nucleotide in the adapter, on the basis of the terminal region of the adapter ligated with the DNA fragment. Here, the first nucleotide in the terminal region of the adapter is the endmost nucleotide present at the position ligated with the DNA fragment, and may refer to: i) a nucleotide at the 5' end of the adapter sequence, adjacent to adenine present at the 3' end of a target DNA fragment; and a nucleotide of the adapter sequence adjacent (linked) to thymine at the 3' end of the adapter sequence, including a nucleotide sequence (thymine) complementary to adenine present at the 3' end of the DNA fragment.

In a specific embodiment, the method, which targets a plurality of DNA fragments, may include a plurality of adapters, and thus the adapter may include different barcode sequences according to the type of DNA fragment.

In a specific embodiment, with regard to the barcode sequence, the first sequence in the adapter may be one of A, T, C, and G, on the basis of the terminal region of the adapter ligated with the DNA fragment, or when the barcode sequence has a length of 2 nt to 10 nt, the second sequence in the adapter may be either C or G, on the basis of the terminal region of the adapter ligated with the DNA fragment. In addition, when the barcode sequence has a length of 2 nt to 10 nt, on the basis of the terminal region of the adapter ligated with the DNA fragment, the first sequence in the adapter is fixed with one of A, T, C, and G, and the adapter My second sequence may be fixed with either C or G.

According to an embodiment, as shown in FIG. 4, when an adapter containing an erroneous barcode sequence acts as a primer in the PCR amplification process, the barcode sequence having the arrangement and the adapter sequence including the same may interrupt, on their own, erroneous replication and amplification processes through a proofing process of DNA polymerase I, in which replication is interrupted by 3'→5' exonuclease activity, thereby reducing the conventional molecular barcoding switching phenomenon.

In another aspect, provided is a composition for preparing a DNA library for nucleic acid sequencing, the composition comprising a plurality of adapters having a length of 40 to 100 nt, including a barcode sequence and a complementary sequence to a primer for a polymerase chain reaction, wherein each of the plurality of adapters includes a different barcode sequence according to the type of DNA fragment, and the barcode sequence has a length of 1 nt to 10 nt, and is arranged to include, on the basis of the terminal region of the adapter ligated with the DNA fragment, the position of a first nucleotide in the adapter.

The composition for preparing a DNA library for nucleic acid sequencing includes or uses the technical configuration used in the method for preparing the DNA library or molecular barcoding method as it is, and description of common content between the two will be omitted.

Specifically, as used herein, "a composition for preparing a DNA library" may be used interchangeably with a kit for preparing a DNA library or an adapter composition for preparing a DNA library.

In a specific embodiment, the composition is for nucleic acid sequencing, and may target a plurality of DNA fragments. Accordingly, the composition may include a plurality of adapters, and thus the adapter may include different barcode sequences according to the type of DNA fragment.

The adapter may include a sequence complementary to a primer for a polymerase chain reaction and a barcode sequence. Here, the sequence complementary to the primer is for initiating or performing a PCR amplification process, and a known or arbitrary primer and a sequence complementary thereto may be applied in a non-limiting manner.

In a specific embodiment, as described above, the barcode sequence may be arranged to include the position of a first nucleotide in the adapter, on the basis of the terminal region of the adapter ligated with the DNA fragment. In addition, with regard to the barcode sequence, the first sequence in the adapter may be one of A, T, C, and G, on the basis of the terminal region of the adapter ligated with the DNA fragment, or when the barcode sequence has a length of 2 nt to 10 nt, the second sequence in the adapter may be either C or G, on the basis of the terminal region of the adapter ligated with the DNA fragment. In addition, when the barcode sequence has a length of 2 nt to 10 nt, on the basis of the terminal region of the adapter ligated with the DNA fragment, the first sequence in the adapter is fixed with one of A, T, C, and G, and the adapter My second sequence may be fixed with either C or G. The composition for preparing a DNA library may include the barcode sequence or a plurality of adapters including the barcode sequence, and the plurality of adapters according to an embodiment may include, for example, based on the total adapters, 90% or more of all adapters, for example, it may be included at a level of 91% or more, 92% or more, 92% or more, 93% or more, 94% or more, 95% or more, 96% or more, 97% or more, 98% or more, 99% or more.

According to an embodiment, a barcode sequence having a conventional arrangement or an adapter sequence comprising the same exhibited a molecular barcode switching ratio of about 6% to 50%, whereas the adapter sequence according to an embodiment was confirmed to have a molecular barcode switching ratio, that is, an error rate, of less than 1 Since the sensitivity and specificity of variant detection can be increased during nucleic acid sequencing, for example, genetic variant detection, the adapter sequence according to an embodiment can be widely used in the field of precision medical-based diagnosis/treatment technology.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 14 is a diagram schematically showing a structure of an adapter to which a position of a barcode sequence and a barcode sequence are fixed according to an embodiment;

DETAILED DESCRIPTION

Figure 1:
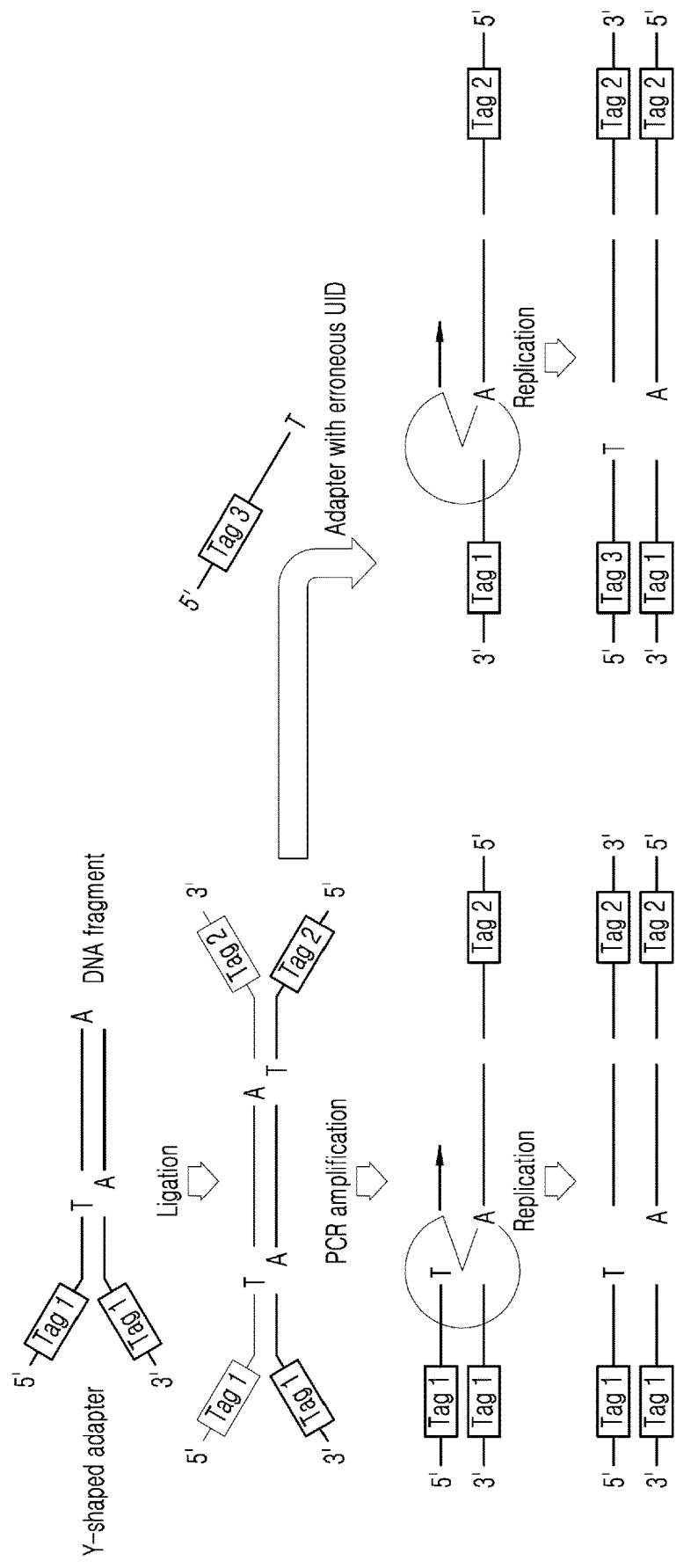
FIG. 1 is a diagram schematically showing the problems of the conventional molecular bar coding technology.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, preferred examples are presented to help the understanding of the present disclosure. However, the following examples are only provided for easier understanding of the present disclosure, and the contents of the present disclosure are not limited by the following examples.

EXAMPLES

Example 1. Confirmation of Possible Errors due to Molecular Barcode Switching

In this example, it was attempted to confirm the possibility of errors due to molecular barcode switching, which may occur during the PCR amplification process. Conventional genomic analysis technology requires random DNA fragmentation and a sequencing process with high depth, and thus there is a risk of losing effective genetic information in the process of amplifying and selecting a large amount of DNA fragments. Therefore, in the art, the error caused by this problem is minimized through molecular barcode technology including a process of ligating an adapter including a specific barcode sequence to a DNA fragment. However, in the conventional molecular barcoding technology as well, as shown in FIG. 1, an adapter containing an erroneous barcode sequence acts as a primer in a subsequent PCR reaction and generates an erroneous PCR copy in the PCR amplification process, resulting in reductions of detection sensitivity and specificity (molecular barcode switching phenomenon), that is, technical limitations still exist.

Figure 2:
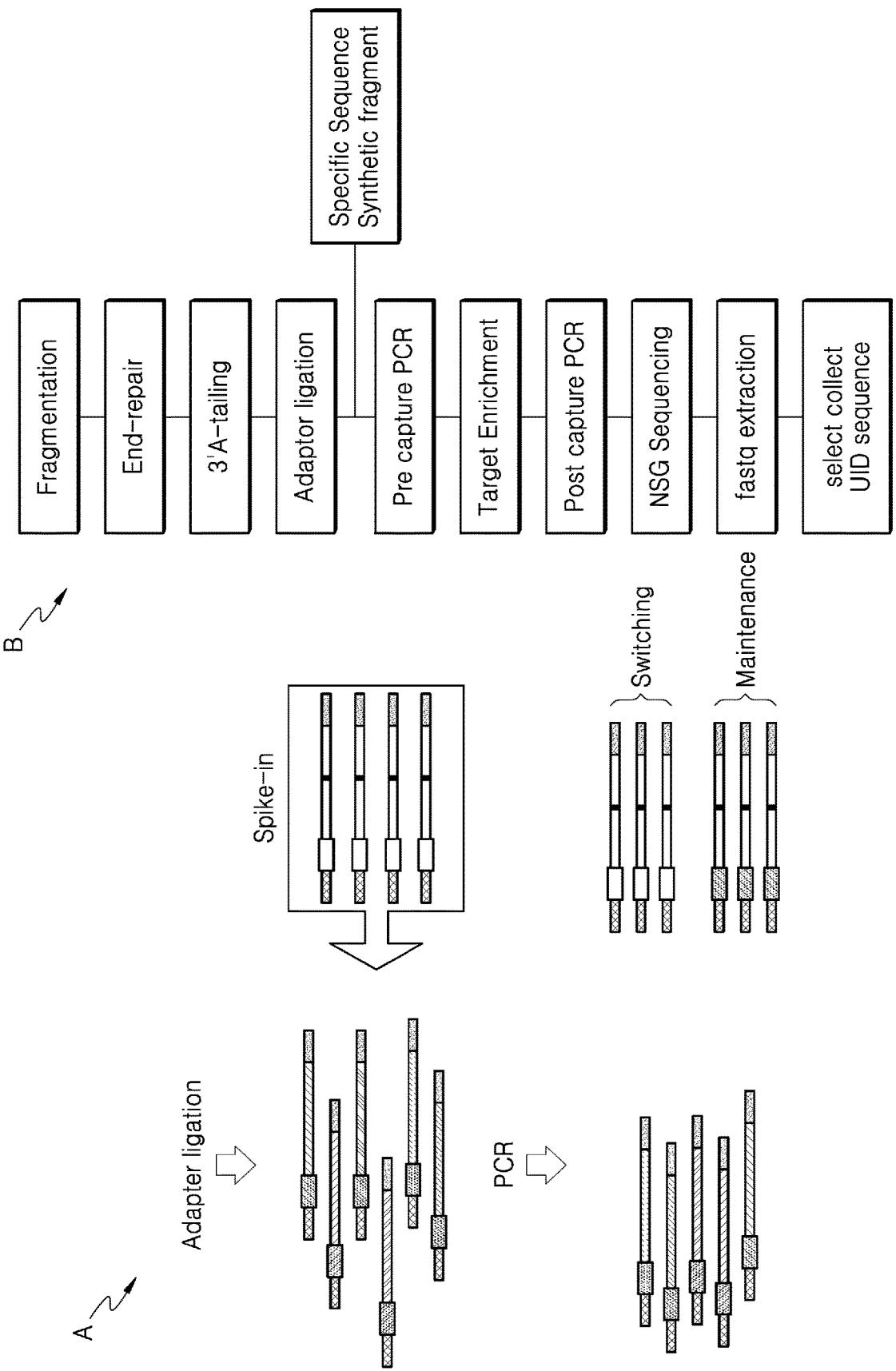
FIG. 2 is a diagram schematically showing an experimental process for inducing a molecular barcode switching phenomenon and a product resulting therefrom.

In this embodiment, as shown in FIG. 2A, it was attempted to experimentally identify problems of the prior art. First, some of nucleotide sequences of five genes KRAS, IDH1, BRCA1, ALK, and ERBB2 were secured by using human reference genome information, and then a 'CTTC' sequence was added to the end of the sequence. Thereafter, while adding an adapter sequence in the form of a library that can be used with Illumina (IllUIDna) sequencer to each nucleotide sequence, an adapter-attached DNA was synthesized in the form in which a specific sequence (AGTC) was fixed at the position of the barcode sequence in the adapter sequence. The information on each of the nucleotide sequences is shown in Table 1 below.

TABLE 1

| Gene | Sequence (5' -> 3') | UID |
|---|---|---|
| KRAS | CTTCATCCTGAGAAGGGAGAAACACAGTCTGGAT<br>TATTACAGTGCACCTTTTACTTCAAAAAAGGTGT<br>TATATACAACTCAACAACAAAAAATTCAATTTAA<br>AAATGGGCAAAGGACTTGAAAAGACATTGTTCCT<br>GCTCCAAAGACTTC | AGTC |
| IDH1 | CTTCAATGGCTTCTCTGAAGACCGTGCCACCCAG<br>AATATTTCGTATGGTGCCATTTGGTGATTTCCAC<br>ATTTGTTTCAACTTGAACTCCTCAACCCTCTTCT<br>CATCAGGAGTGATAGTGGCACATTTGACGCCAAC<br>ATTATGCTTCCTTC | AGTC |
| BRCA1 | CTTCTTCTGGCTTCTCCCTGCTCACACTTTCTTC<br>CATTGCATTATACCCAGCAGTATCAGTAGTATGA<br>GCAGCAGCTGGACTCTGGGCAGATTCTGCAACTT<br>TCAACTTTCAATTGGGGAACTTTCAATGCAGAGG<br>TTGAAGATGGCTTC | AGTC |
| ALK | CTTCACTGATGGAGGAGGTCTTGCCAGCAAAGCA<br>GTAGTTGGGGTTGTAGTCGGTCATGATGGTCGAG<br>GTGCGGAGCTTGCTCAGCTTGTACTCAGGGCTCT<br>GCAGCTCCATCTGCATGGCTTGCAGCTCCTGGTG<br>CTTCCGGCGGCTTC | AGTC |
| ERBB2 | CTTCGCTACGTGCTCATCGCTCACAACCAAGTGA<br>GGCAGGTCCCACTGCAGAGGCTGCGGATTGTGCG<br>AGGCACCCAGCTCTTTGAGGACAACTATGCCCTG<br>GCCGTGCTAGACAATGGAGACCCGCTGAACAATA<br>CCACCCCTGTCTTC | AGTC |

Meanwhile, in order to simulate the process in which the adapter containing the erroneous barcode sequence acts in the PCR amplification process, a nucleotide sequence having an artificial variation sequence introduced into a target sequence was additionally synthesized, and in this example, the nucleotide sequence was referred to as a specific sequence synthesis fragment or a spike-in fragment. Then, as shown in FIG. 2B, after ligating 50 ng of input DNA and 1.8×SPRI, a series of experiments, including a PCR amplification process to which purification conditions were applied, were performed, and as the result, the ratio of spike-in fragments among all of the amplified fragments was calculated. Specifically, the ratio of the spike-in fragments was compared according to the number of purifications (one or two) and the adapter concentration (50 ng or 5 ng).

Figure 3:
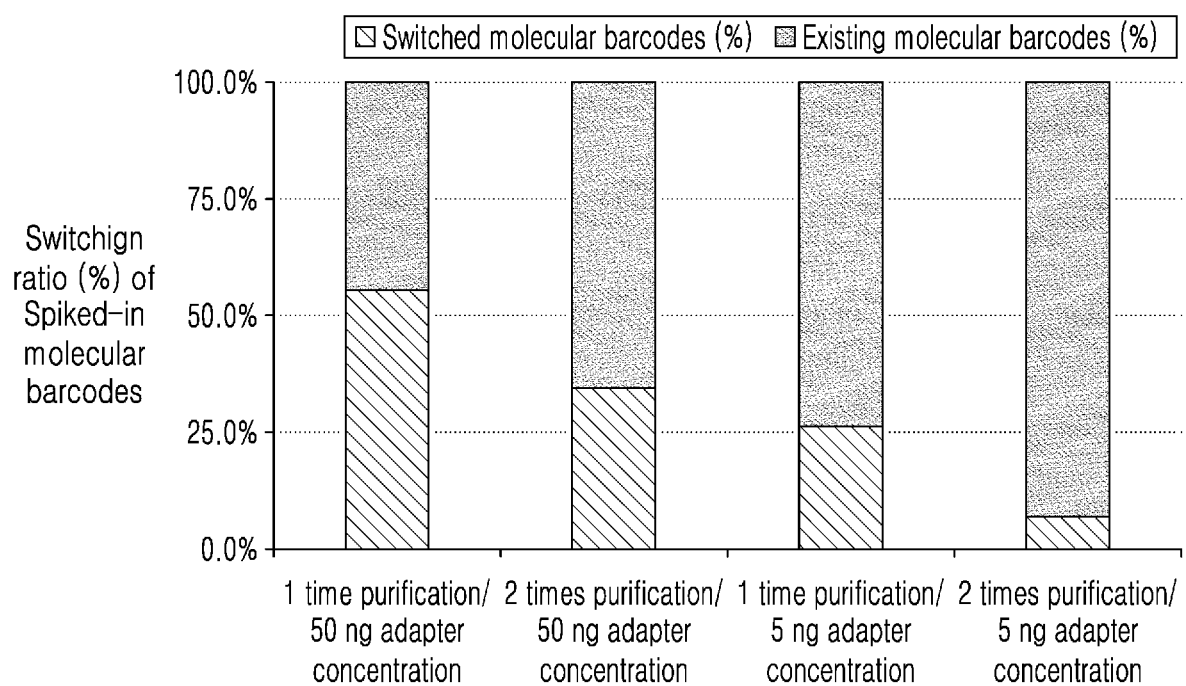
FIG. 3 shows results of confirming the switching ratio of molecular barcodes according to the number of purifications and the adapter concentration in the PCR amplification process to which the conventional molecular barcoding technology is applied.

FIG. 3 shows results of confirming the switching ratio of molecular barcodes according to the number of purifications and the concentration of adapters in the PCR amplification process to which the existing molecular barcoding technology is applied.

As a result, as shown in FIG. 3, the spike-in fragments occupied about 6% to 50% of the total molecular barcodes according to the experimental conditions, and specifically, as the number of purifications decreased, and/or the concentration of adapters including the barcode sequence increased, the ratio of spike-in fragments tended to increase.

These experimental results indicate that there is a possibility of causing errors in the genomic analysis results because molecular barcoding switching may occur when the adapter including the barcode sequence is not completely removed in the purification process but acts as a primer during pre-PCR, in the existing molecular barcoding technology.

Figure 4:
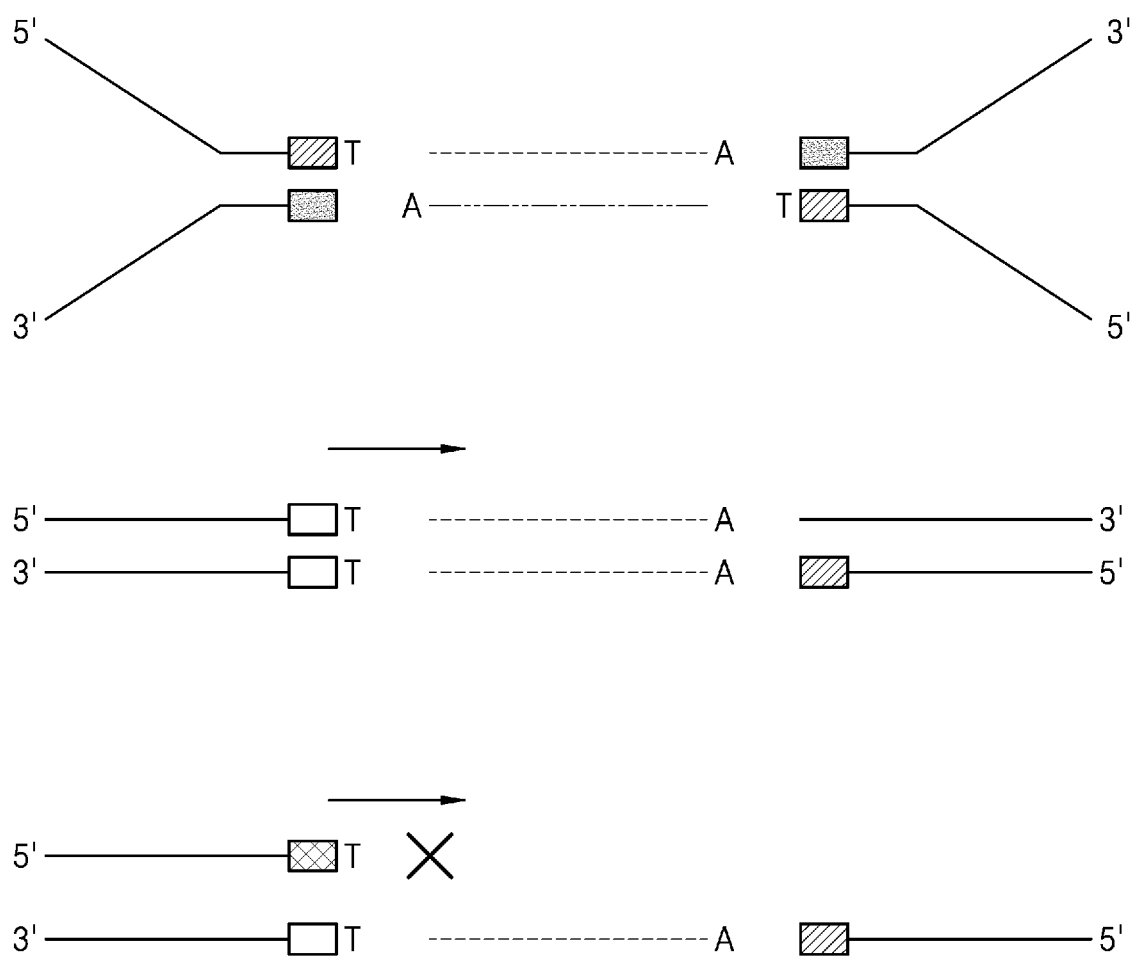
FIG. 4 is a diagram schematically showing a series of processes for reducing molecular barcoding switching in an adapter and a PCR amplification process using the same according to an embodiment.

Example 2. Confirmation of Molecular Barcode Switching Reducing Effect According to Position of Barcode Sequence In this example, an adapter structure in which a barcode sequence is fixed at a terminal region of the adapter was designed, and through this, it was attempted to confirm whether the problems of the prior art mentioned in Example 1 could be solved. Specifically, as shown in FIG. 4, it was attempted to confirm whether the existing molecular barcode switching phenomena could be reduced in the PCR amplification process to which the adapter sequence of this example is applied through a proofing process of DNA polymerase I, in which replication is interrupted by 3'→5' exonuclease activity, when an adapter containing an erroneous barcode sequence acts as a primer.

Figure 5:
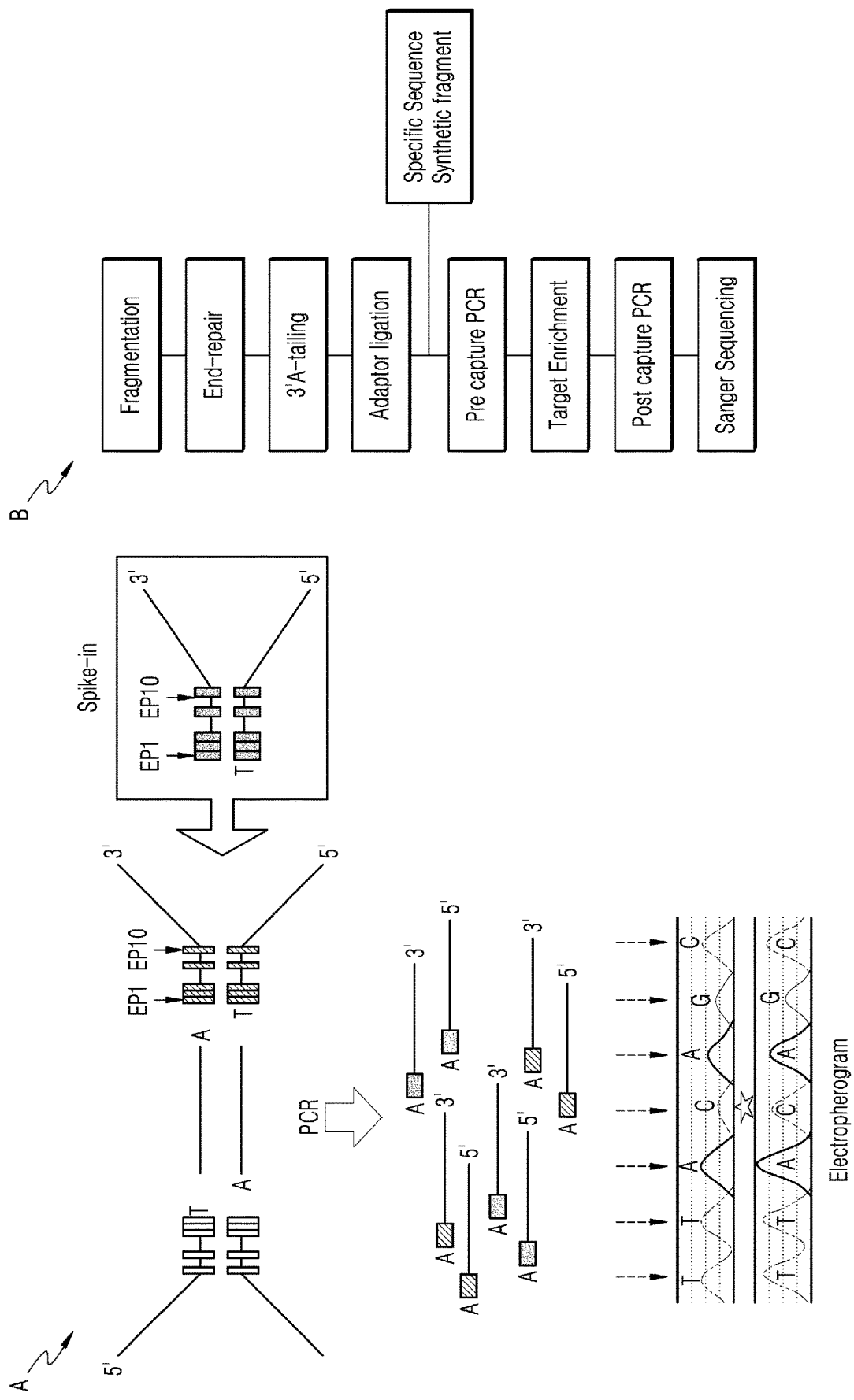
FIG. 5 is a diagram schematically showing an experimental procedure for evaluating the level of molecular barcoding switching in the PCR amplification process using an adapter in which the barcode sequence according to an embodiment is fixed at a terminal region of the adapter.

To this end, as shown in the A region of FIG. 5, first, the adapter was designed for the barcode sequence to be located in the terminal region of the adapter, where ligation with the DNA fragment is performed. More specifically, the adapter was prepared in such a manner that the adapter-endmost nucleotide position at which ligation with the DNA fragment was performed was set to a first end point (EP1), and on the basis of the EP1, the second, third, fifth, or tenth end point was set to EP2, EP3, EP5, or EP10, respectively. Then, these regions were fixed with A , T, G, or C. In addition, specific sequence synthesis fragments or spike-in adapters were synthesized in which the corresponding sequence at a fixed position in the barcode sequence was changed (replaced) with another nucleotide. Next, as shown in the B portion of FIG. 5, a series of experiments, including a PCR amplification process to which conditions of some of 10 ng plasmid DNAs, 1.0 uM index adaptor working concentration, and 0.1 uM spike-in working concentration, were applied, were performed, and sequencing peaks were identified by using an imageJ program, and then the molecular barcode switching ratio was calculated according to Equation 1 below. Meanwhile, in this experiment, the control group was set as a group to which the spike-in adapter into which the changed sequence was introduced was not applied.

$$\text{Molecular barcode switching (\%)} = \frac{\text{Amount of } DNA \text{ fragments fixed at spike-in adapter}}{\text{Amount of } DNA \text{ fragments fixed at ligated adapter}} \quad \text{[Equation 1]}$$

Figure 6:
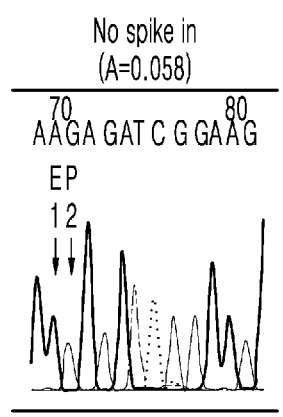
FIG. 6 shows results of confirming the level of molecular barcoding switching in the PCR amplification process using an adapter in which the barcode sequence according to an embodiment is fixed at a terminal region of the adapter.
Figure 7:
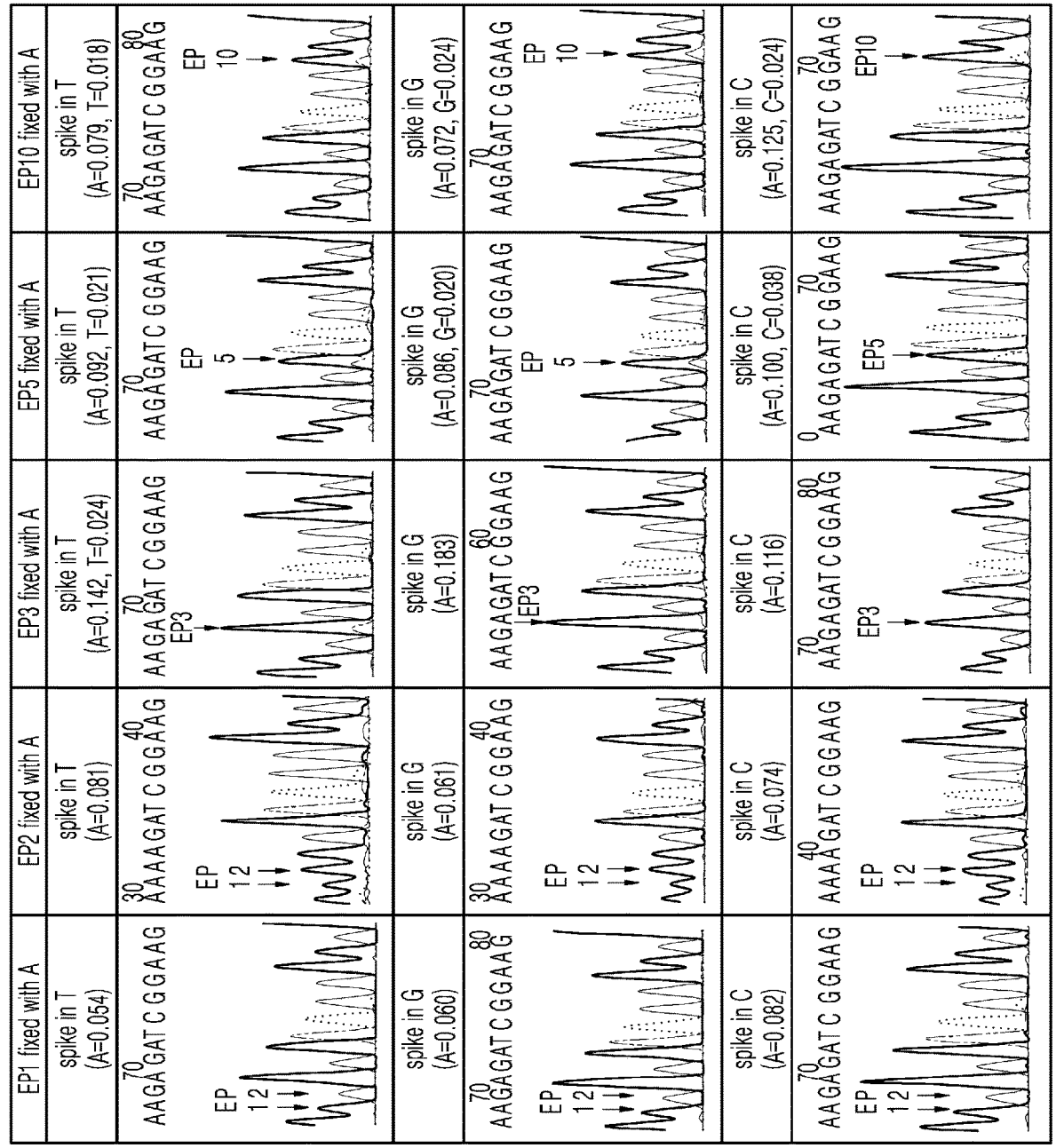
FIG. 7 shows results of confirming the level of molecular barcoding switching when a specific position in the barcode sequence is fixed with adenine (A) in the PCR amplification process using an adapter in which the barcode sequence according to an embodiment is fixed at a terminal region of the adapter.
Figure 8:
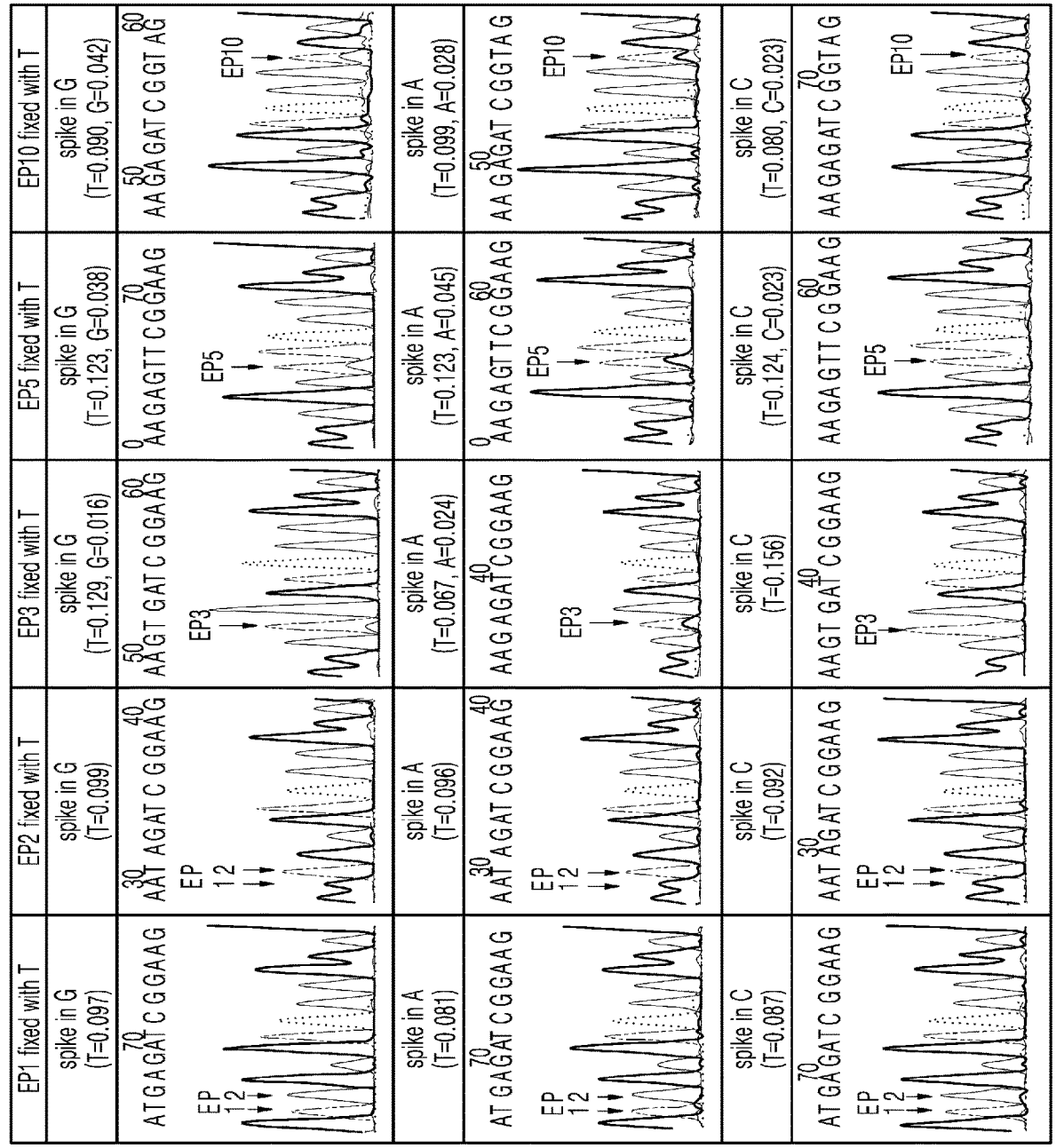
FIG. 8 shows results of confirming the level of molecular barcoding switching when a specific position in the barcode sequence is fixed with thymine (T) in the PCR amplification process using an adapter in which the barcode sequence according to an embodiment is fixed at a terminal region of the adapter.
Figure 9:
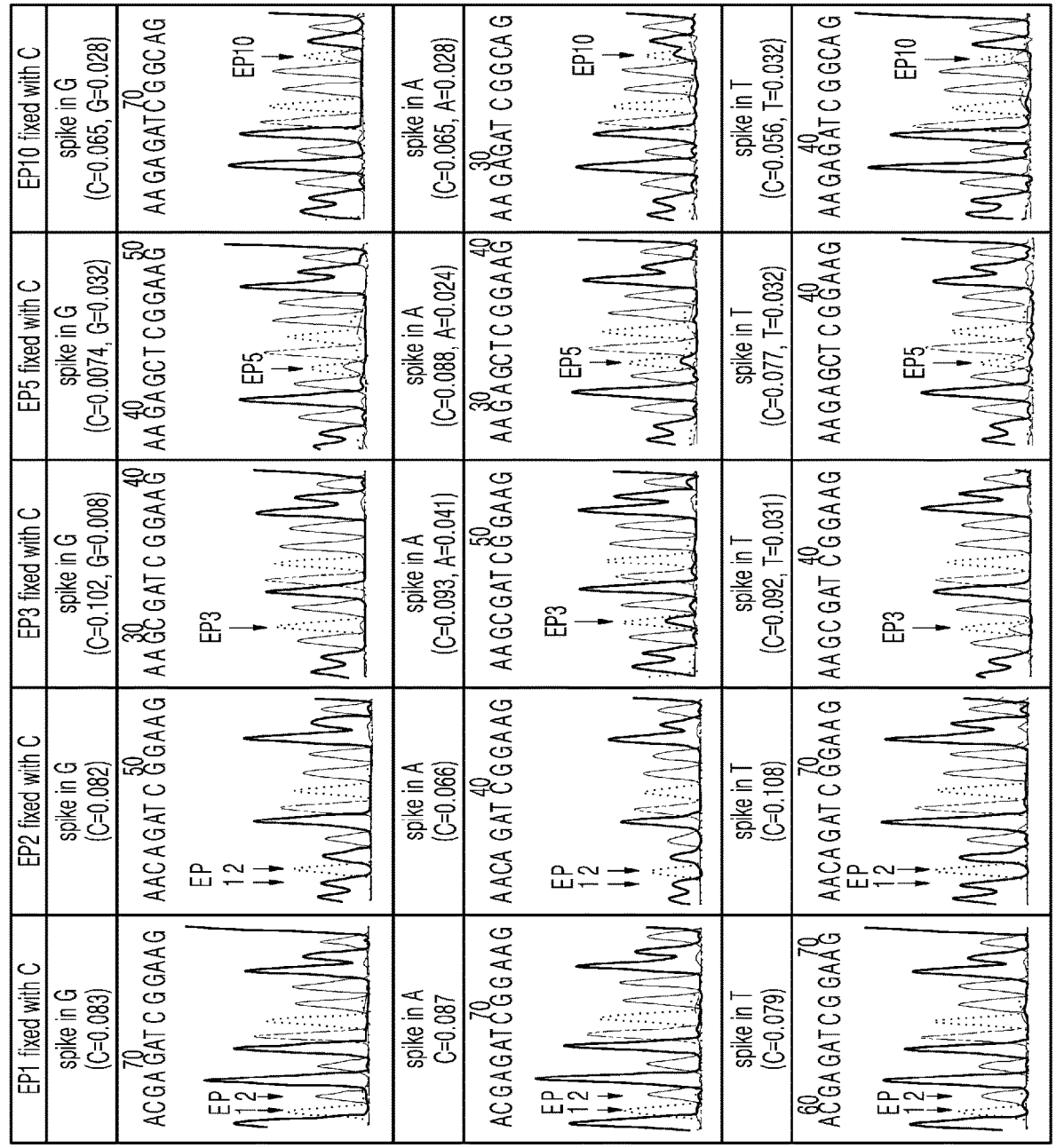
FIG. 9 shows results of confirming the level of molecular barcoding switching when a specific position in the barcode sequence is fixed with cytosine (C) in the PCR amplification process using an adapter in which the barcode sequence according to an embodiment is fixed at a terminal region of the adapter.
Figure 10:
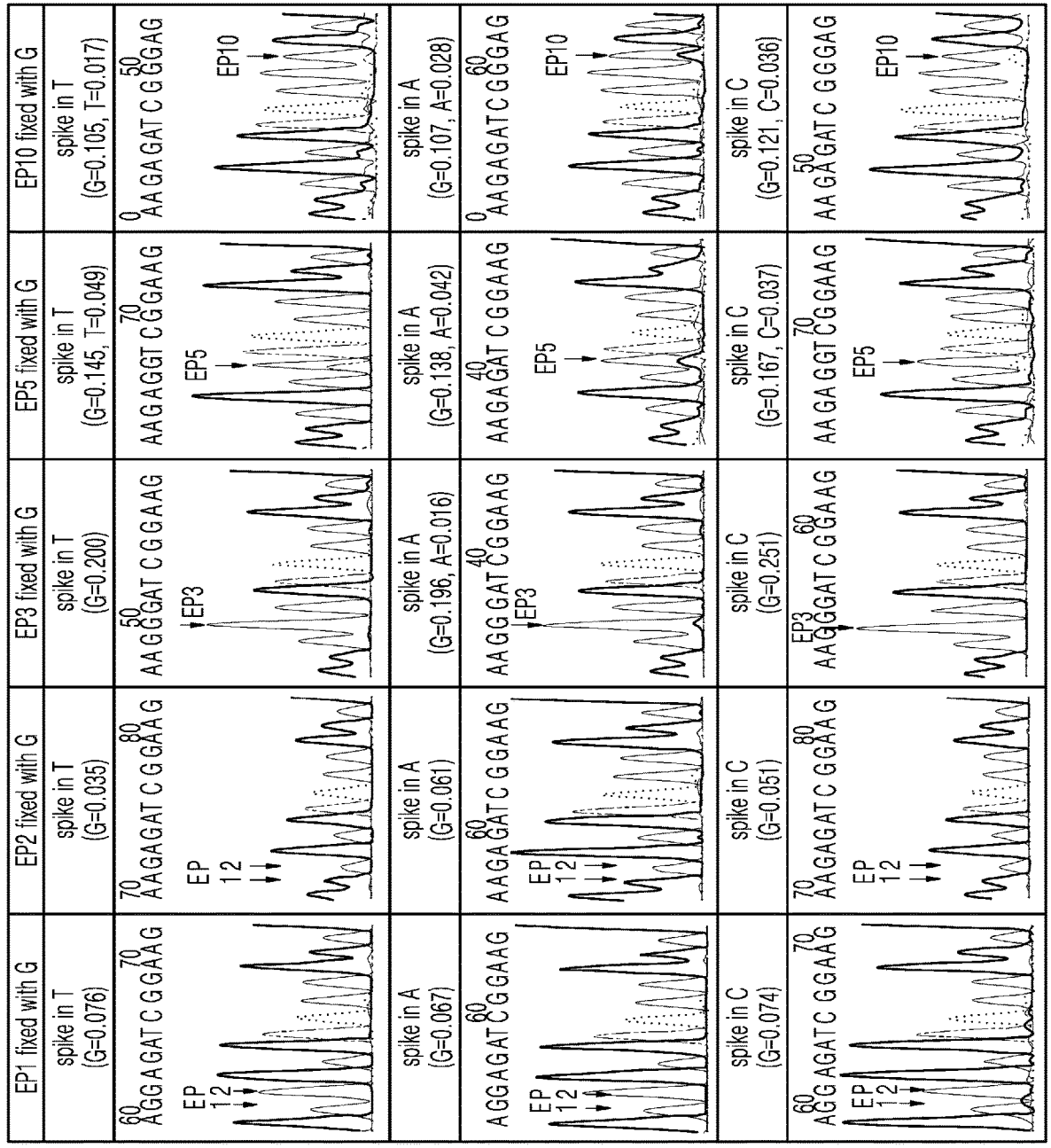
FIG. 10 shows results of confirming the level of molecular barcoding switching when a specific position in the barcode sequence is fixed with guanine (G) in the PCR amplification process using an adapter in which the barcode sequence according to an embodiment is fixed at a terminal region of the adapter.
Figure 11:
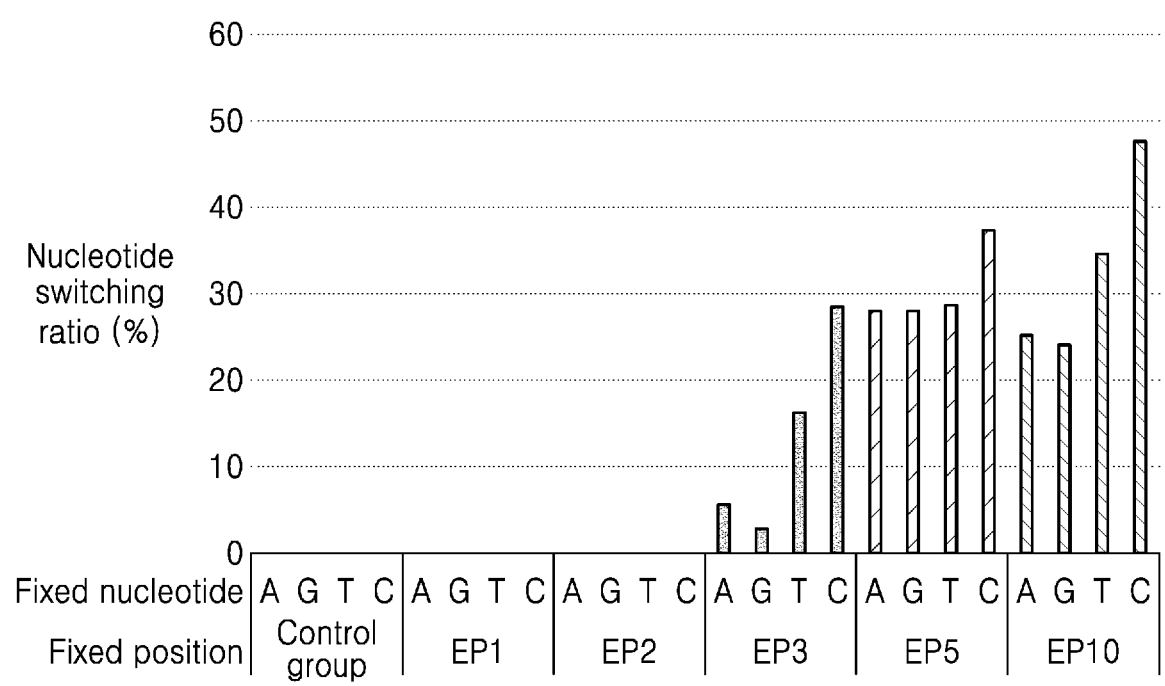
FIG. 11 shows results of confirming the level of molecular barcoding switching according to a specific position and a fixed nucleotide sequence when the specific position in the barcode sequence and a nucleotide sequence thereof are fixed in the PCR amplification process using an adapter in which the barcode sequence according to an embodiment is fixed at a terminal region of the adapter.

FIG. 6 shows results of confirming the level of molecular barcoding switching in the PCR amplification process using an adapter in which the barcode sequence according to an embodiment is fixed at a terminal region of the adapter. As a result, as shown in FIG. 6 , in the EP1 region, it was confirmed that the level of detection of three types of nucleotide sequences other than the originally designed nucleotide sequence was very low (A=0.058).

In addition, Table 2 and FIGS. 7 to 11 indicate molecular barcoding switching levels according to a specific position and a fixed nucleotide sequence, when a specific position in the barcode sequence and a nucleotide sequence thereof were fixed in the PCR amplification process using an adapter in which the barcode sequence according to an embodiment is fixed at a terminal region of the adapter.

TABLE 2

| Fixed position | Nucleotide type | | Detected amount | | Turnover rate (%) | Average turnover rate (%) |
|---|---|---|---|---|---|---|
| | Ligation | spike-in | Ligation | spike-in | | |
| Control | | | 0.058 | | 0 | 0 |
| | | | >LOD | | 0 | 0 |
| | | | >LOD | | 0 | 0 |
| | | | >LOD | | 0 | 0 |
| EP1 | A | G | 0.06 | | 0% | 0% |
| | A | T | 0.054 | | 0% | |
| | A | C | 0.082 | | 0% | |
| | G | A | 0.067 | | 0% | 0% |
| | G | T | 0.076 | | 0% | |
| | G | C | 0.074 | | 0% | |
| | T | G | 0.097 | | 0% | 0% |
| | T | A | 0.081 | | 0% | |
| | T | C | 0.087 | | 0% | |
| | C | G | 0.083 | | 0% | 0% |
| | C | A | 0.087 | | 0% | |
| | C | T | 0.079 | | 0% | |
| EP2 | A | G | 0.061 | | 0% | 0% |
| | A | T | 0.081 | | 0% | |
| | A | C | 0.074 | | 0% | |
| | G | A | 0.061 | | 0% | 0% |
| | G | T | 0.035 | | 0% | |
| | G | C | 0.051 | | 0% | |
| | T | G | 0.099 | | 0% | 0% |
| | T | A | 0.096 | | 0% | |
| | T | C | 0.092 | | 0% | |
| | C | G | 0.082 | | 0% | 0% |
| | C | A | 0.066 | | 0% | |
| | C | T | 0.108 | | 0% | |
| EP3 | A | G | 0.183 | 0.024 | 0% | 6% |
| | A | T | 0.142 | | 17% | |
| | A | C | 0.116 | | 0% | |
| | G | A | 0.196 | 0.016 | 8% | 3% |
| | G | T | 0.2 | | 0% | |
| | G | C | 0.251 | | 0% | |
| | T | G | 0.129 | 0.016 | 12% | 16% |
| | T | A | 0.067 | 0.024 | 36% | |
| | T | C | 0.156 | | 0% | |
| | C | G | 0.102 | 0.008 | 8% | 29% |
| | C | A | 0.093 | 0.041 | 44% | |
| | C | T | 0.092 | 0.031 | 34% | |
| EP5 | A | G | 0.086 | 0.02 | 23% | 28% |
| | A | T | 0.092 | 0.021 | 23% | |
| | A | C | 0.1 | 0.038 | 38% | |
| | G | A | 0.138 | 0.042 | 30% | 29% |
| | G | T | 0.145 | 0.049 | 34% | |
| | G | C | 0.167 | 0.037 | 22% | |
| | T | G | 0.123 | 0.038 | 31% | 29% |
| | T | A | 0.123 | 0.045 | 37% | |
| | T | C | 0.124 | 0.023 | 19% | |
| | C | G | 0.074 | 0.032 | 43% | 37% |
| | C | A | 0.088 | 0.024 | 27% | |
| | C | T | 0.077 | 0.032 | 42% | |
| EP10 | A | G | 0.072 | 0.024 | 33% | 25% |
| | A | T | 0.079 | 0.018 | 23% | |
| | A | C | 0.125 | 0.024 | 19% | |
| | G | A | 0.107 | 0.028 | 26% | 24% |
| | G | T | 0.105 | 0.017 | 16% | |
| | G | C | 0.121 | 0.036 | 30% | |
| | T | G | 0.09 | 0.042 | 47% | 35% |
| | T | A | 0.099 | 0.028 | 28% | |
| | T | C | 0.08 | 0.023 | 29% | |
| | C | G | 0.065 | 0.028 | 43% | 48% |
| | C | A | 0.065 | 0.028 | 43% | |
| | C | T | 0.056 | 0.032 | 57% | |

As a result, as shown in Table 2 and FIGS. 7 to 11, no molecular barcode switching was detected at the positions EP1 and EP2, whereas the molecular barcode switching ratio tended to increase as the distance from the terminal region of the adapter where ligation with the DNA fragment was performed was increased. Specifically, this tendency was evidently shown from the EP3 position, and after EP3, when cytosine (C) was introduced, the molecular barcode switching ratio was further increased.

These experimental results indicate that when the barcode sequence is present in the terminal region of the adapter, for example, in the region including the EP1 and EP2 positions, molecular barcode switching occurring in the PCR amplification process can be reduced.

Example 3. Confirmation of Molecular Barcode Switching Reducing Effect according to Position of Nucleotide Sequence In this example, an adapter structure in which a barcode sequence is fixed at a terminal region of the adapter was designed, and through this, it was attempted to confirm whether the problems of the prior art mentioned in Example 1 could be solved.

3-1. First End Point (EP1) in Adapter

The EP1 region was fixed with A, C, G, or T, respectively, and the EP2 region was set to C or G to synthesize and prepare a designed barcode sequence and an adapter sequence including the same, and after performing the experiment in the same procedure as in Example 2, the ratio of adapters in which the barcode sequence did not change, that is, the ratio in which molecular barcode switching did not occur, was calculated.

Table 3 shows the results when the EP1 position in the barcode sequence was fixed with adenine (A).

TABLE 3

| | | EP2 Read Pos 1 | EP1 Read Pos 2 | A(%) |
|---|---|---|---|---|
| Control | Index 1 | C | A | 99.62% |
| | Index 2 | G | A | |
| | Spike-in 1 | — | — | |
| | Spike-in 2 | — | — | |
| 1 | Index 1 | C | A | 99.53% |
| | Index 2 | G | A | |
| | Spike-in 1 | C | C | |
| | Spike-in 2 | G | C | |
| 2 | Index 1 | C | A | 99.44% |
| | Index 2 | G | A | |
| | Spike-in 1 | C | T | |
| | Spike-in 2 | G | T | |
| 3 | Index 1 | C | A | 98.28% |
| | Index 2 | G | A | |
| | Spike-in 1 | C | G | |
| | Spike-in 2 | G | G | |

Table 4 shows the results when the EP1 position in the barcode sequence was fixed with cytosine (C).

TABLE 4

| | | EP2 Read Pos 1 | EP1 Read Pos 2 | C(%) |
|---|---|---|---|---|
| Control | Index 1 | C | C | 99.68% |
| | Index 2 | G | C | |
| | Spike-in 1 | — | — | |
| | Spike-in 2 | — | — | |
| 1 | Index 1 | C | C | 99.14% |
| | Index 2 | G | C | |
| | Spike-in 1 | C | T | |
| | Spike-in 2 | G | T | |
| 2 | Index 1 | C | C | 99.57% |
| | Index 2 | G | C | |
| | Spike-in 1 | C | G | |
| | Spike-in 2 | G | G | |

TABLE 4-continued

|   | | EP2<br>Read Pos 1 | EP1<br>Read Pos 2 | C(%) |
|---|---|---|---|---|
| 3 | Index 1 | C | C | 99.66% |
|   | Index 2 | G | C | |
|   | Spike-in 1 | C | A | |
|   | Spike-in 2 | G | A | |

Table 5 shows the results when the EP1 region in the barcode sequence was fixed with guanine (G).

TABLE 5

|   | | EP2<br>Read Pos 1 | EP1<br>Read Pos 2 | G(%) |
|---|---|---|---|---|
| Control | Index 1 | C | G | 99.64% |
|   | Index 2 | G | G | |
|   | Spike-in 1 | — | — | |
|   | Spike-in 2 | — | — | |
| 1 | Index 1 | C | G | 99.67% |
|   | Index 2 | G | G | |
|   | Spike-in 1 | C | C | |
|   | Spike-in 2 | G | C | |
| 2 | Index 1 | C | G | 99.53% |
|   | Index 2 | G | G | |
|   | Spike-in 1 | C | T | |
|   | Spike-in 2 | G | T | |
| 3 | Index 1 | C | G | 99.50% |
|   | Index 2 | G | G | |
|   | Spike-in 1 | C | A | |
|   | Spike-in 2 | G | A | |

Table 6 shows the results when the EP1 position in the barcode sequence was fixed with thymine (T).

TABLE 6

|   | | EP2<br>Read Pos 1 | EP1<br>Read Pos 2 | T(%) |
|---|---|---|---|---|
| Control | Index 1 | C | T | 99.56% |
|   | Index 2 | G | T | |
|   | Spike-in 1 | — | — | |
|   | Spike-in 2 | — | — | |
| 1 | Index 1 | C | T | 99.43% |
|   | Index 2 | G | T | |
|   | Spike-in 1 | C | C | |
|   | Spike-in 2 | G | C | |
| 2 | Index 1 | C | T | 99.50% |
|   | Index 2 | G | T | |
|   | Spike-in 1 | C | G | |
|   | Spike-in 2 | G | G | |
| 3 | Index 1 | C | T | 99.53% |
|   | Index 2 | G | T | |
|   | Spike-in 1 | C | A | |
|   | Spike-in 2 | G | A | |

Figure 12:
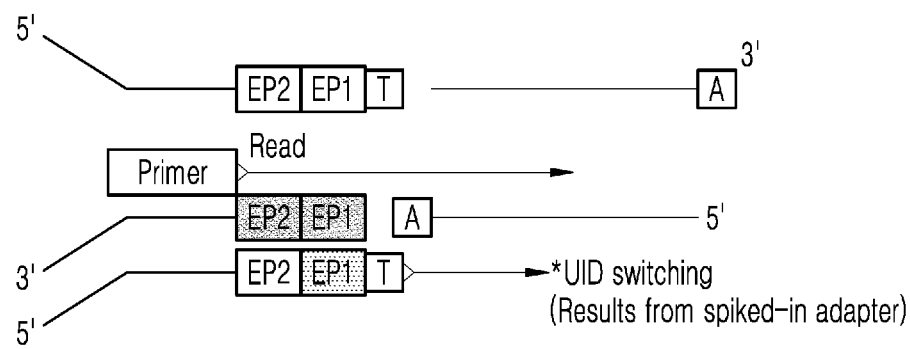
FIG. 12 shows results of confirming the level of molecular barcoding switching according to the fixation of an adapter-end first nucleotide sequence (EP1) in the PCR amplification process using an adapter in which the barcode sequence according to an embodiment is fixed at a terminal region of the adapter.
Figure 12:
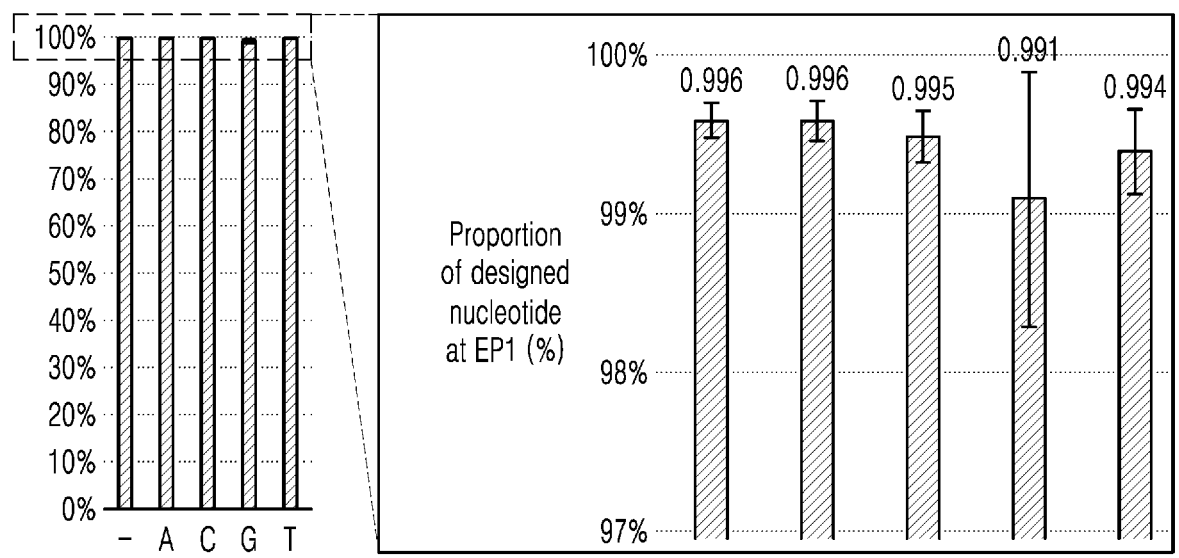

FIG. 12 shows results of confirming the level of molecular barcoding switching according to the fixation of an adapter-end first nucleotide sequence in the PCR amplification process using an adapter in which the barcode sequence according to an embodiment is fixed at a terminal region of the adapter. As a result, as shown in FIG. 12, it was confirmed that the barcode switching ratio, that is, the error rate, was less than 1% regardless of the type of the nucleotide sequence fixed at the EP1 region.

3-2. Second End Point (EP2) in Adapter

The EP2 region was fixed with A, C, G, or T, respectively, and the EP1 region was set to C, T, G, or A to synthesize and prepare a designed barcode sequence and an adapter sequence including the same, and after performing the experiment in the same procedure as in Example 2, the ratio of adapters in which the barcode sequence did not change, that is, the ratio in which molecular barcode switching did not occur, was calculated.

Tables 7 and 8 show the results when the EP2 position in the barcode sequence was fixed with cytosine (C).

TABLE 7

|   | | EP2<br>Read Pos 1 | EP1<br>Read Pos 2 | C(%) |
|---|---|---|---|---|
| Control | Index 1 | C | C | 99.787% |
|   | Index 2 | C | T | |
|   | Index 3 | C | G | |
|   | Index 4 | C | A | |
|   | Spike-in 1 | — | — | |
|   | Spike-in 2 | — | — | |
|   | Spike-in 3 | — | — | |
|   | Spike-in 4 | — | — | |
| 1 | Index 1 | C | C | 99.044% |
|   | Index 2 | C | T | |
|   | Index 3 | C | G | |
|   | Index 4 | C | A | |
|   | Spike-in 1 | G | C | |
|   | Spike-in 2 | G | T | |
|   | Spike-in 3 | G | G | |
|   | Spike-in 4 | G | A | |

TABLE 8

|   | | EP2<br>Read Pos 1 | EP1<br>Read Pos 2 | C(%) |
|---|---|---|---|---|
| control | Index 1 | C | C | 99.167% |
|   | Index 2 | C | T | |
|   | Index 3 | C | G | |
|   | Index 4 | C | A | |
|   | Spike-in 1 | — | — | |
|   | Spike-in 2 | — | — | |
|   | Spike-in 3 | — | — | |
|   | Spike-in 4 | — | — | |
| 1 | Index 1 | C | C | 98.963% |
|   | Index 2 | C | T | |
|   | Index 3 | C | G | |
|   | Index 4 | C | A | |
|   | Spike-in 1 | G | C | |
|   | Spike-in 2 | G | T | |
|   | Spike-in 3 | G | G | |
|   | Spike-in 4 | G | A | |

Tables 9 and 10 show the results when the EP2 position in the barcode sequence was fixed with guanine (G).

TABLE 9

|   | | EP2<br>Read Pos 1 | EP1<br>Read Pos 2 | G(%) |
|---|---|---|---|---|
| Control | Index 1 | G | C | 99.262% |
|   | Index 2 | G | T | |
|   | Index 3 | G | G | |
|   | Index 4 | G | A | |
|   | Spike-in 1 | — | — | |
|   | Spike-in 2 | — | — | |
|   | Spike-in 3 | — | — | |
|   | Spike-in 4 | — | — | |
| 1 | Index 1 | G | C | 99.234% |
|   | Index 2 | G | T | |
|   | Index 3 | G | G | |
|   | Index 4 | G | A | |
|   | Spike-in 1 | C | C | |
|   | Spike-in 2 | C | T | |

TABLE 9-continued

|  | EP2 Read Pos 1 | EP1 Read Pos 2 | G(%) |
|---|---|---|---|
| Spike-in 3 | C | G |  |
| Spike-in 4 | C | A |  |

TABLE 10

|  |  | EP2 Read Pos 1 | EP1 Read Pos 2 | C(%) |
|---|---|---|---|---|
| Control | Index 1 | G | C | 99.311% |
|  | Index 2 | G | T |  |
|  | Index 3 | G | G |  |
|  | Index 4 | G | A |  |
|  | Spike-in 1 | — | — |  |
|  | Spike-in 2 | — | — |  |
|  | Spike-in 3 | — | — |  |
|  | Spike-in 4 | — | — |  |
| 1 | Index 1 | G | C | 99.259% |
|  | Index 2 | G | T |  |
|  | Index 3 | G | G |  |
|  | Index 4 | G | A |  |
|  | Spike-in 1 | C | C |  |
|  | Spike-in 2 | C | T |  |
|  | Spike-in 3 | C | G |  |
|  | Spike-in 4 | C | A |  |

Figure 13:
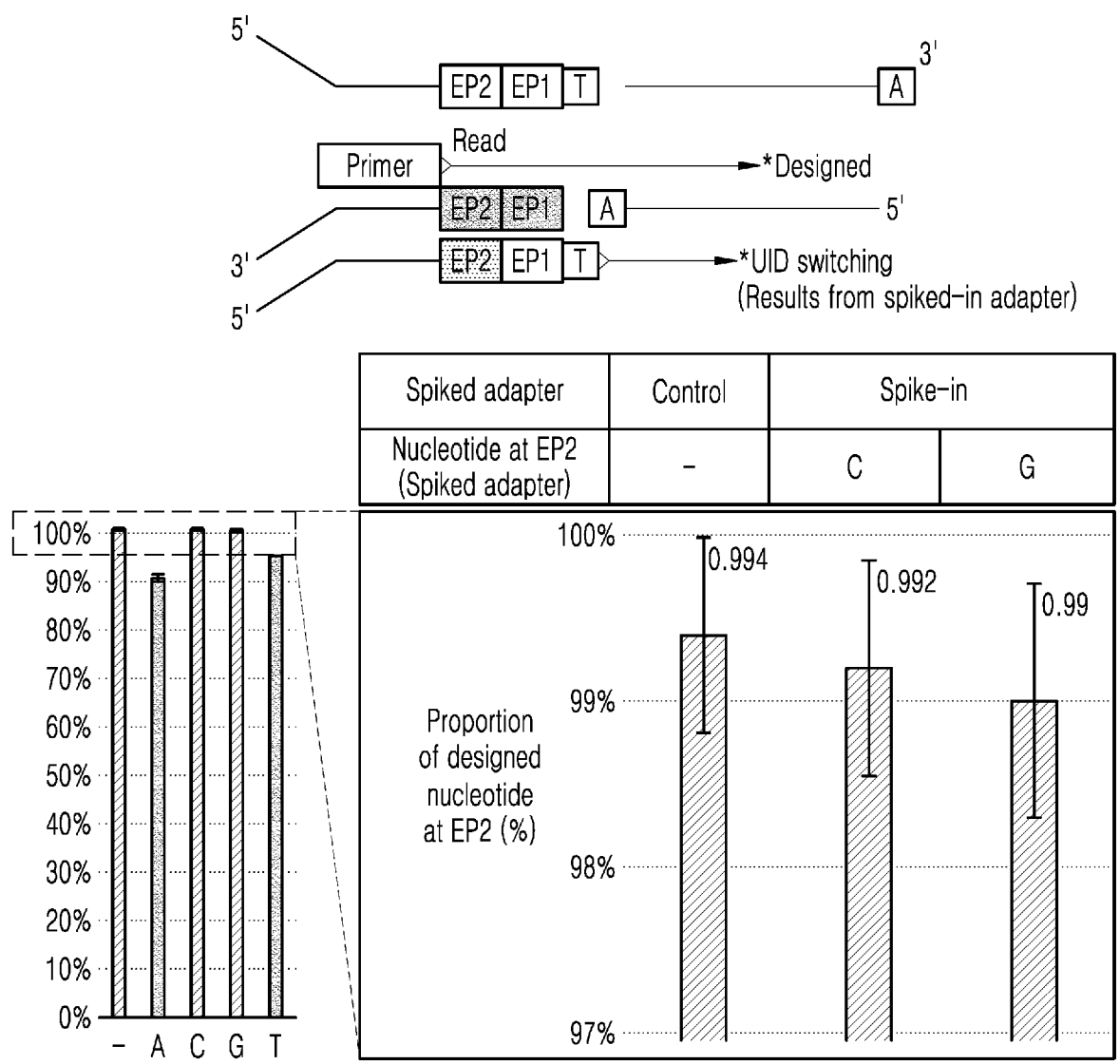
FIG. 13 shows results of confirming the level of molecular barcoding switching according to the fixation of an adapter-end second nucleotide sequence (EP2) in the PCR amplification process using an adapter (UDI) in which the barcode sequence according to an embodiment is fixed at a terminal region of the adapter.

FIG. 13 shows results of confirming the level of molecular barcoding switching according to the fixation of an adapter-end second nucleotide sequence (EP2) in the PCR amplification process using an adapter in which the barcode sequence according to an embodiment is fixed at a terminal region of the adapter. As a result, as shown in FIG. 13, it was confirmed that when the nucleotide sequence fixed at the EP2 region was C or G, the molecular barcode switching ratio, that is, the error rate, was less than 1%.

These experimental results indicate that the adapter including the barcode sequence according to an embodiment can reduce molecular barcoding and, specifically, can contribute to improving the sensitivity and specificity of variant detection in the process of detecting genetic variants through sequencing, and thus can be widely in the precision medical-based diagnosis/treatment technology.

Example 4. Verification of Molecular barcoding switching Reducing Effect and Evaluation of Variant Detection Accuracy In this example, based on the experimental results of Example 3, it was attempted to verify whether the fixation of the EP1 sequence could reduce molecular barcoding switching, thus improving the accuracy of variant detection in an adapter structure in which the barcoding position was fixed at a terminal region of the adapter, where DNA fragmentation and ligation were performed.

4-1. Evaluation of Duplicate Family Size Ratio

By using an adapter including a molecular barcode designed by fixing the EP1 region to A, C, G, or T, and setting the EP2 region to C or G (UDI: Unique Dual Identifier, Table 11), and an adapter including a conventional barcode (UMI: Unique Molecular Identifier, Table 12), the experiment was performed in the same procedure as in Example 2, and then the ratio of duplicate family sizes generated when each barcode was used was calculated. In Tables 11 and 12, the bolded portions indicate the barcode sequences according to an embodiment, and the underlined portions are regions additionally introduced for demultiplexing products resulting after sequencing in this example and then separating the same for each sequence corresponding to each sample. In addition, the adapter was designed such that the sequence data, that is, the read, generated by DNA polymerase I included sequences complementary to the barcode sequence at a terminal region of the adapter, for example, UDI_CC_index_D_A01_i7 would be amplified from the GG region at the 5' end position. In addition, FIG. 14 is a diagram schematically illustrating the structure of an adapter to which the position of the barcode sequence and the barcode sequence are fixed according to an embodiment (UDI_CC_index_D_A01_i7 and UDI_CC_index_D_A01_i5 in Table 11).

TABLE 11

| Oligo_Name | Sequence |
|---|---|
| UDI_CC_index_D_A01_i7 | /5Phos/GGAGATCGGAAGAGCACACGTCTGAACTCCAGTCAC<u>CCGGAACGAAA</u>TCTCGTATGCCGTCTTCTGCTTG |
| UDI_CC_index_D_A01_i5 | AATGATACGGCGACCACCGAGATCTACAC<u>CTAC</u>ACTATGACACTCTTTCCCTACACGACGCTCTTC<u>CGATCT</u>CCT |
| UDI_TC_index_D_A01_i7 | /5Phos/AGAGATCGGAAGAGCACACGTCTGAACTCCAGTCAC<u>CCGGAACGAAA</u>TCTCGTATGCCGTCTTCTGCTTG |
| UDI_TC_index_D_A01_i5 | AATGATACGGCGACCACCGAGATCTACAC<u>CTAC</u>ACTATGACACTCTTTCCCTACACGACGCTCTTC<u>CGATCT</u>CTT |
| UDI_GC_index_D_A01_i7 | /5Phos/CGAGATCGGAAGAGCACACGTCTGAACTCCAGTCAC<u>CCGGAACGAAA</u>TCTCGTATGCCGTCTTCTGCTTG |
| UDI_GC_index_D_A01_i5 | AATGATACGGCGACCACCGAGATCTACAC<u>CTAC</u>ACTATGACACTCTTTCCCTACACGACGCTCTTC<u>CGATCT</u>CGT |
| UDI_AC_index_D_A01_i7 | /5Phos/TGAGATCGGAAGAGCACACGTCTGAACTCCAGTCAC<u>CCGGAACGAAA</u>TCTCGTATGCCGTCTTCTGCTTG |
| UDI_AC_index_D_A01_i5 | AATGATACGGCGACCACCGAGATCTACAC<u>CTAC</u>ACTATGACACTCTTTCCCTACACGACGCTCTTC<u>CGATCT</u>CAT |
| UDI_CG_index_D_A01_i7 | /5Phos/GCAGATCGGAAGAGCACACGTCTGAACTCCAGTCAC<u>CCGGAACGAAA</u>TCTCGTATGCCGTCTTCTGCTTG |
| UDI_CG_index_D_A01_i5 | AATGATACGGCGACCACCGAGATCTACAC<u>CTAC</u>ACTATGACACTCTTTCCCTACACGACGCTCTTC<u>CGATCT</u>GCT |
| UDI_TG_index_D_A01_i7 | /5Phos/ACAGATCGGAAGAGCACACGTCTGAACTCCAGTCAC<u>CCGGAACGAAA</u>TCTCGTATGCCGTCTTCTGCTTG |
| UDI_TG_index_D_A01_i5 | AATGATACGGCGACCACCGAGATCTACAC<u>CTAC</u>ACTATGACACTCTTTCCCTACACGACGCTCTTC<u>CGATCT</u>GTT |
| UDI_GG_index_D_A01_i7 | /5Phos/CCAGATCGGAAGAGCACACGTCTGAACTCCAGTCAC<u>CCGGAACGAAA</u>TCTCGTATGCCGTCTTCTGCTTG |
| UDI_GG_index_D_A01_i5 | AATGATACGGCGACCACCGAGATCTACAC<u>CTAC</u>ACTATGACACTCTTTCCCTACACGACGCTCTTC<u>CGATCT</u>GGT |

TABLE 11-continued

| Oligo_Name | Sequence |
| --- | --- |
| UDI_AG_index_D_A01_i7 | /5Phos/TCAGATCGGAAGAGCACACGTCTGAACTCCAGTCAC<u>CCGGAACGAA</u>ATCTCGTATGCCGTCTTCTGCTTG |
| UDI_AG_index_D_A01_i5 | AATGATACGGCGACCACCGAGATCTACAC<u>CTAC</u><u>ACTATGCA</u>CTCTTTCCCTACACGACGCTCTTCCGATCTGAT |

TABLE 12

| OligoName | Sequence |
| --- | --- |
| Adaptor-universal-UMI-i5 | AATGATACGGCGACCACCGAGATCTACACTCTTTCCCTACACGACGCTCTTCCGATCT |
| UMI_Index_1 | GATCGGAAGAGCACACGTCTGAACTCCAGTCAC<u>ATGCCTAA</u>ATCTCGTATGCCGTCTTCTGCTTG |
| UMI_Index_2 | GATCGGAAGAGCACACGTCTGAACTCCAGTCAC<u>GAATCTGA</u>ATCTCGTATGCCGTCTTCTGCTTG |
| UMI_Index_3 | GATCGGAAGAGCACACGTCTGAACTCCAGTCAC<u>AACGTGAT</u>ATCTCGTATGCCGTCTTCTGCTTG |
| UMI_Index_4 | GATCGGAAGAGCACACGTCTGAACTCCAGTCAC<u>CACTTCGA</u>ATCTCGTATGCCGTCTTCTGCTTG |
| UMI_Index_5 | GATCGGAAGAGCACACGTCTGAACTCCAGTCAC<u>GCCAAGAC</u>ATCTCGTATGCCGTCTTCTGCTTG |
| UMI_Index_6 | GATCGGAAGAGCACACGTCTGAACTCCAGTCAC<u>GACTAGTA</u>ATCTCGTATGCCGTCTTCTGCTTG |
| UMI_Index_7 | GATCGGAAGAGCACACGTCTGAACTCCAGTCAC<u>ATTGGCTC</u>ATCTCGTATGCCGTCTTCTGCTTG |
| UMI_Index_8 | GATCGGAAGAGCACACGTCTGAACTCCAGTCAC<u>GATGAATC</u>ATCTCGTATGCCGTCTTCTGCTTG |
| UMI_Index_9 | GATCGGAAGAGCACACGTCTGAACTCCAGTCAC<u>AGCAGGAA</u>ATCTCGTATGCCGTCTTCTGCTTG |
| UMI_Index_10 | GATCGGAAGAGCACACGTCTGAACTCCAGTCAC<u>GAGCTGAA</u>ATCTCGTATGCCGTCTTCTGCTTG |
| UMI_Index_11 | GATCGGAAGAGCACACGTCTGAACTCCAGTCAC<u>AAACATCG</u>ATCTCGTATGCCGTCTTCTGCTTG |
| UMI_Index_12 | GATCGGAAGAGCACACGTCTGAACTCCAGTCAC<u>GAGTTAGC</u>ATCTCGTATGCCGTCTTCTGCTTG |
| UMI_Index_13 | GATCGGAAGAGCACACGTCTGAACTCCAGTCAC<u>CGAACTTA</u>ATCTCGTATGCCGTCTTCTGCTTG |
| UMI_Index_14 | GATCGGAAGAGCACACGTCTGAACTCCAGTCAC<u>GATAGACA</u>ATCTCGTATGCCGTCTTCTGCTTG |
| UMI_Index_15 | GATCGGAAGAGCACACGTCTGAACTCCAGTCAC<u>AAGGACAC</u>ATCTCGTATGCCGTCTTCTGCTTG |
| UMI_Index_16 | GATCGGAAGAGCACACGTCTGAACTCCAGTCAC<u>GACAGTGC</u>ATCTCGTATGCCGTCTTCTGCTTG |
| UMI_Index_17 | GATCGGAAGAGCACACGTCTGAACTCCAGTCAC<u>ATCATTCC</u>ATCTCGTATGCCGTCTTCTGCTTG |
| UMI_Index_18 | GATCGGAAGAGCACACGTCTGAACTCCAGTCAC<u>GCCACATA</u>ATCTCGTATGCCGTCTTCTGCTTG |
| UMI_Index_19 | GATCGGAAGAGCACACGTCTGAACTCCAGTCAC<u>ACCACTGT</u>ATCTCGTATGCCGTCTTCTGCTTG |

TABLE 12-continued

| OligoName | Sequence |
| --- | --- |
| UMI_Index_20 | GATCGGAAGAGCACACGTCTGAACTCCAGTCAC<u>CTGGCATA</u>ATCTCGTATGCCGTCTTCTGCTTG |
| UMI_Index_21 | GATCGGAAGAGCACACGTCTGAACTCCAGTCAC<u>ACCTCCAA</u>ATCTCGTATGCCGTCTTCTGCTTG |
| UMI_Index_22 | GATCGGAAGAGCACACGTCTGAACTCCAGTCAC<u>GCGAGTAA</u>ATCTCGTATGCCGTCTTCTGCTTG |
| UMI_Index_23 | GATCGGAAGAGCACACGTCTGAACTCCAGTCAC<u>ACTATGCA</u>ATCTCGTATGCCGTCTTCTGCTTG |
| UMI_Index_24 | GATCGGAAGAGCACACGTCTGAACTCCAGTCAC<u>CGGATTGC</u>ATCTCGTATGCCGTCTTCTGCTTG |
| UMI_Index_25 | GATCGGAAGAGCACACGTCTGAACTCCAGTCAC<u>AACTCACC</u>ATCTCGTATGCCGTCTTCTGCTTG |
| UMI_Index_26 | GATCGGAAGAGCACACGTCTGAACTCCAGTCAC<u>GCTAACGA</u>ATCTCGTATGCCGTCTTCTGCTTG |
| UMI_Index_27 | GATCGGAAGAGCACACGTCTGAACTCCAGTCAC<u>CAGATCTG</u>ATCTCGTATGCCGTCTTCTGCTTG |
| UMI_Index_28 | GATCGGAAGAGCACACGTCTGAACTCCAGTCAC<u>ATCCTGTA</u>ATCTCGTATGCCGTCTTCTGCTTG |
| UMI_Index_29 | GATCGGAAGAGCACACGTCTGAACTCCAGTCAC<u>CTGTAGCC</u>ATCTCGTATGCCGTCTTCTGCTTG |
| UMI_Index_30 | GATCGGAAGAGCACACGTCTGAACTCCAGTCAC<u>GCTCGGTA</u>ATCTCGTATGCCGTCTTCTGCTTG |
| UMI_Index_31 | GATCGGAAGAGCACACGTCTGAACTCCAGTCAC<u>ACACGACC</u>ATCTCGTATGCCGTCTTCTGCTTG |
| UMI_Index_32 | GATCGGAAGAGCACACGTCTGAACTCCAGTCAC<u>AGTCACTA</u>ATCTCGTATGCCGTCTTCTGCTTG |

Meanwhile, in the amplification process through PCR, the sequence data derived from duplicated DNA fragments are grouped to generate one consensus each. Here, the number of read pairs having a unique barcode sequence is to be referred to as a family size, and when the family size becomes small, a possibility of analysis errors may increase, and thus there is a risk that the accuracy of variant detection may be reduced. Based on this, in the PCR amplification process using an adapter (UDI) in which the barcode sequence according to an embodiment is fixed at a terminal region of the adapter, the confirmation results of the duplicate family size ratio according to the fixation of an adapter-end nucleotide sequence are shown in FIG. 15.

Figure 15:
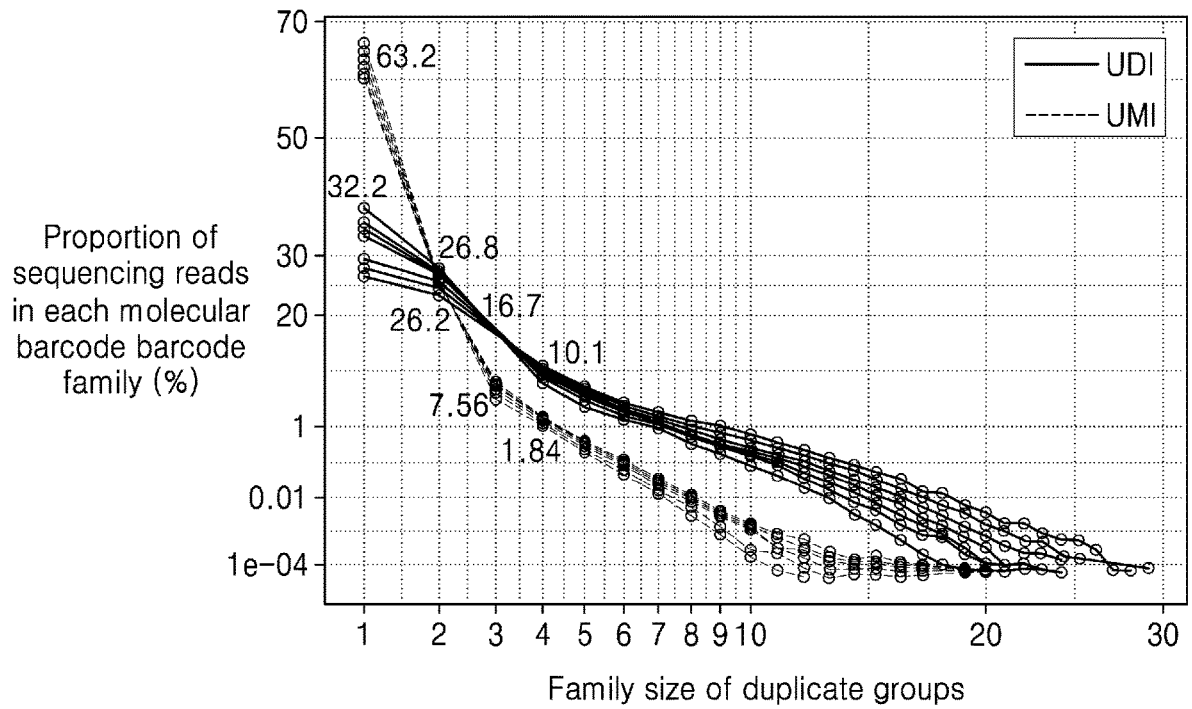
FIG. 15 shows results of confirming the duplicate family size ratio according to the fixation of an adapter-end nucleotide sequence in the PCR amplification process using an adapter (UDI) in which the barcode sequence according to an embodiment is fixed at a terminal region of the adapter.

As a result, as shown in FIG. 15, when the conventional adapter (UMI) was used, compared to the case where the adapter according to an embodiment (UDI) was used, the ratio of singletons having a family size of 1 was observed to be very high. Combining with the previous experimental results, it is determined that this is due to an error caused by the molecular barcode switching phenomenon. That is, from the experimental results, it was found that when the adapter including the barcode sequence according to an embodiment was used in the PCR amplification process, the molecular barcode switching error of 31.0% of the total data was corrected compared to the previous experimental results.

4-2. Evaluation of Accuracy of Variant Detection

By using 8 standard materials containing variants at 0.1%, 0.5%, and 1.0% levels, it was attempted to confirm whether the accuracy of variant detection was actually improved when using an adapter having the position of the barcode sequence according to an embodiment and an adapter having fixation of a specific sequence. To this end, a total of 9 standard material libraries were designed by using the UDI and UMI of Example 4-1 by generating 3 repeat samples for each variant concentration. As shown in Table 13, in order to evaluate how consistently the variants were detected, a total of 72 test groups were set up, the experiment was performed in the same manner as in Example 2, the level of variants contained in the standard materials were compared to the proportion at which reads containing variants were not generated, and then the variances of the detected variants were compared.

Figure 16:
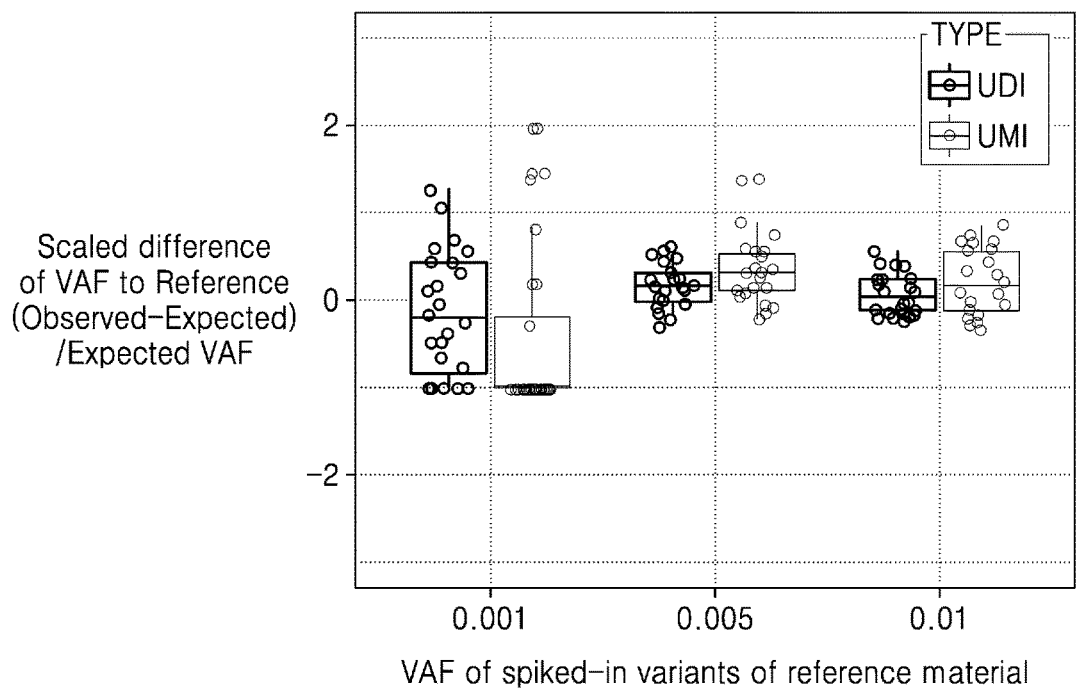
FIG. 16 shows results of confirming the variance of VAFs of variants detected according to the fixation of an adapter-end nucleotide sequence in the PCR amplification process using an adapter (UDI) in which the barcode sequence according to an embodiment is fixed at a terminal region of the adapter.

As a result, as shown in Tables 13 and 14, it was confirmed that when UDI was used, no read was generated in 6 out of 72 variants (ND: non-detectable), and when UMI was used, no read was generated in 17 out of 72 variants. In addition, as shown in FIG. 16 and Table 15, it was confirmed that the variance of the VAF of the variants detected in the data produced using UDI was small, and this difference was statistically significant (P-value>0.05). Specifically, in evaluating the accuracy of variant detection at the 0.1 level, UMI had unsequenced supporting reads for 17 out of 24, that is, 71% variations, whereas UDI had 6 out of 24, that is, 25% variations. These experimental results indicate that the detection accuracy for a low-level variation can be improved in the case of using the barcode sequence according to an embodiment, compared to the case of using the conventional UMI.

TABLE 15

| VAF (Reference variant) | SD | | P value (F-test; "one-side") |
|---|---|---|---|
| | UDI | UMI | |
| 0.001 | 0.000708 | 0.000942 | 0.09 |
| 0.005 | 0.00127 | 0.00178 | 0.05 |
| 0.01 | 0.00234 | 0.00375 | 0.01 |

In the method and composition according to an aspect, molecular barcode switching phenomena, which has been pointed out as a problem in the prior art, can be reduced, and thus the molecular barcoding accuracy and the false-positive variant removal rate can be significantly improved.

In the method and composition according to an aspect, since the sensitivity and specificity of variant detection can be increased in the process of detecting genetic mutations, the accuracy of genome sequencing-based treatment and diagnosis can be greatly improved.

TABLE 13

| Sample information | | | | SNV | | | | INDEL | |
|---|---|---|---|---|---|---|---|---|---|
| | | | | | | | | EGFR | |
| Customer | % | EGFR | EGFR | KRAS | NRAS | NRAS | PIK3CA | ΔE746-A750 | EGFR |
| UMI | 0.10% | ND | ND | 0.244% | 0.238% | ND | 0.070% | ND | ND |
| | 0.10% | 0.180% | ND | ND | 0.118% | ND | 0.118% | ND | ND |
| | 0.10% | ND | ND | 0.299% | ND | ND | ND | ND | ND |
| | 0.50% | 0.557% | 0.694% | 0.697% | 0.754% | 0.784% | 0.624% | 1.190% | 0.512% |
| | 0.50% | 0.456% | 0.946% | 0.662% | 0.651% | 0.391% | 0.535% | 0.678% | 0.571% |
| | 0.50% | 0.436% | 0.789% | 0.779% | 0.654% | 0.860% | 0.648% | 0.468% | 0.565% |
| | 1.00% | 0.831% | 1.216% | 1.861% | 1.675% | 1.080% | 1.726% | 0.962% | 0.983% |
| | 1.00% | 0.669% | 1.290% | 1.661% | 0.799% | 1.546% | 1.602% | 0.700% | 0.897% |
| | 1.00% | 1.344% | 0.937% | 1.427% | 1.054% | 1.214% | 1.692% | 0.781% | 0.792% |
| UDI | 0.10% | 0.145% | ND | 0.096% | 0.168% | ND | 0.075% | 0.144% | 0.132% |
| | 0.10% | 0.021% | ND | 0.083% | 0.062% | 0.033% | 0.157% | 0.115% | 0.050% |
| | 0.10% | ND | ND | 0.156% | 0.226% | 0.205% | 0.111% | 0.051% | ND |
| | 0.50% | 0.621% | 0.775% | 0.732% | 0.536% | 0.421% | 0.565% | 0.485% | 0.511% |
| | 0.50% | 0.497% | 0.753% | 0.586% | 0.809% | 0.682% | 0.652% | 0.575% | 0.376% |
| | 0.50% | 0.341% | 0.437% | 0.606% | 0.626% | 0.542% | 0.746% | 0.610% | 0.492% |
| | 1.00% | 0.813% | 0.882% | 1.419% | 1.235% | 1.545% | 1.083% | 1.165% | 0.832% |
| | 1.00% | 1.228% | 0.766% | 0.888% | 1.417% | 1.391% | 1.163% | 0.884% | 0.777% |
| | 1.00% | 0.869% | 1.245% | 1.115% | 0.959% | 1.122% | 0.972% | 0.780% | 0.888% |

TABLE 14

| Barcode | Samples (n) | Positive variant detection rate (Sensitivity) | Remark |
|---|---|---|---|
| UDI | 9 | 66/72 (91.7%) | VAF ≥ 0.1% |
| UMI | 9 | 55/72 (76.4%) | VAF ≥ 0.1% |

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method for preparing a DNA library for nucleic acid sequencing, the method comprising:
    ligating an adapter comprising a barcode sequence to both ends of a DNA fragment extracted and fragmented from a target sample;
    separating the ligated DNA fragment into single strands; and
    amplifying the single-stranded DNA fragment ligated with the adapter through a polymerase chain reaction by using a primer that recognizes the adapter,
    wherein the barcode sequence has a length of 2 nt to 10 nt and is arranged to include the position of a first nucleotide in the adapter, on the basis of a terminal region of the adapter ligated with the DNA fragment, and
    wherein the second nucleotide in the adaptor is either G or C.

2. The method of claim 1, wherein the nucleic acid sequencing is next generation sequencing (NGS), targeted sequencing, targeted deep sequencing, or panel sequencing.

3. The method of claim 1, wherein the DNA is a genome or a fragment thereof.

4. The method of claim 1, wherein the adapter has a length of 40 nt to 100 nt, and includes a barcode sequence having a length of 2 nt to 10 nt.

5. The method of claim 1, wherein a plurality of DNA fragments are targeted and a plurality of adapters are used, and the adapters include different barcode sequences according to the type of DNA fragment.

6. The method of claim 5, wherein the barcode sequence has a length of 2 nt to 10 nt, and on the basis of the terminal region of the adapter ligated with a DNA fragment, the first nucleotide in the adapter is fixed with one of A, T, C, and G, and the second nucleotide in the adapter is fixed with either C or G.

7. A molecular barcoding method for nucleic acid sequencing, comprising the step of ligating an adapter comprising a barcode sequence to both ends of a DNA fragment extracted and fragmented from a target sample,
wherein the barcode sequence has a length of 2 nt to 10 nt and is arranged to include the position of a first nucleotide in the adapter, on the basis of a terminal region of the adapter ligated with the DNA fragment, and
wherein the second nucleotide in the adaptor is either G or C.

8. The molecular barcoding method of claim 7, wherein the adapter has a length of 40 nt to 100 nt, and includes a barcode sequence having a length of 2 nt to 10 nt.

9. The molecular barcoding method of claim 7, wherein a plurality of DNA fragments are targeted and a plurality of adapters are used, and the adapters include different barcode sequences according to the type of DNA fragment.

10. The molecular barcoding method of claim 9, wherein the barcode sequence has a length of 2 nt to 10 nt, and on the basis of the terminal region of the adapter ligated with a DNA fragment, the first nucleotide in the adapter is fixed with one of A, T, C, and G, and the second nucleotide in the adapter is fixed with either C or G.

11. The molecular barcoding method of claim 7, before the ligating the adapter, further comprising the steps of:
repairing an end of the DNA fragment extracted and fragmented from the target sample; and
conjugating adenine to the 3' end of the end-repaired DNA fragment.

\* \* \* \* \*

SEQUENCE LISTING

<160> NUMBER OF SEQ ID NOS: 55

<210> SEQ ID NO 1
<211> LENGTH: 150
<212> TYPE: DNA
<213> ORGANISM: Artificial
<220> FEATURE:
<223> OTHER INFORMATION: KRAS

<400> SEQUENCE: 1

```
cttcatcctg agaagggaga aacacagtct ggattattac agtgcacctt ttacttcaaa    60
aaaggtgtta tatacaactc aacaacaaaa aattcaattt aaaaatgggc aaaggacttg   120
aaaagacatt gttcctgctc caaagacttc                                    150
```

<210> SEQ ID NO 2
<211> LENGTH: 150
<212> TYPE: DNA
<213> ORGANISM: Artificial
<220> FEATURE:
<223> OTHER INFORMATION: IDH1

<400> SEQUENCE: 2

```
cttcaatggc ttctctgaag accgtgccac ccagaatatt tcgtatggtg ccatttggtg    60
atttccacat ttgtttcaac ttgaactcct caaccctctt ctcatcagga gtgatagtgg   120
cacatttgac gccaacatta tgcttccttc                                    150
```

<210> SEQ ID NO 3
<211> LENGTH: 150
<212> TYPE: DNA
<213> ORGANISM: Artificial
<220> FEATURE:
<223> OTHER INFORMATION: BRCA1

<400> SEQUENCE: 3

```
cttcttctgg cttctccctg ctcacacttt cttccattgc attataccca gcagtatcag    60
tagtatgagc agcagctgga ctctgggcag attctgcaac tttcaacttt caattgggga   120
actttcaatg cagaggttga agatggcttc                                    150
```

<210> SEQ ID NO 4
<211> LENGTH: 150
<212> TYPE: DNA
<213> ORGANISM: Artificial
<220> FEATURE:
<223> OTHER INFORMATION: ALK

<400> SEQUENCE: 4

```
cttcactgat ggaggaggtc ttgccagcaa agcagtagtt ggggttgtag tcggtcatga    60
tggtcgaggt gcggagcttg ctcagcttgt actcagggct ctgcagctcc atctgcatgg   120
cttgcagctc ctggtgcttc cggcggcttc                                    150
```

<210> SEQ ID NO 5
<211> LENGTH: 150
<212> TYPE: DNA
<213> ORGANISM: Artificial
<220> FEATURE:
<223> OTHER INFORMATION: ERBB2

<400> SEQUENCE: 5

```
cttcgctacg tgctcatcgc tcacaaccaa gtgaggcagg tcccactgca gaggctgcgg    60
attgtgcgag gcacccagct cttttgaggac aactatgccc tggccgtgct agacaatgga  120
```
gacccgctga acaataccac ccctgtcttc                                           150

<210> SEQ ID NO 6
<211> LENGTH: 4
<212> TYPE: DNA
<213> ORGANISM: Artificial
<220> FEATURE:
<223> OTHER INFORMATION: UID

<400> SEQUENCE: 6 agtc                                                                         4

<210> SEQ ID NO 7
<211> LENGTH: 70
<212> TYPE: DNA
<213> ORGANISM: Artificial
<220> FEATURE:
<223> OTHER INFORMATION: UDI_CC_index_D_A01_i7

<400> SEQUENCE: 7
ggagatcgga agagcacacg tctgaactcc agtcacccgg aacgaaatct cgtatgccgt            60
cttctgcttg                                                                  70

<210> SEQ ID NO 8
<211> LENGTH: 75
<212> TYPE: DNA
<213> ORGANISM: Artificial
<220> FEATURE:
<223> OTHER INFORMATION: UDI_CC_index_D_A01_i5

<400> SEQUENCE: 8
aatgatacgg cgaccaccga gatctacacc tacactatga cactctttcc ctacacgacg            60
ctcttccgat ctcct                                                            75

<210> SEQ ID NO 9
<211> LENGTH: 70
<212> TYPE: DNA
<213> ORGANISM: Artificial
<220> FEATURE:
<223> OTHER INFORMATION: UDI_TC_index_D_A01_i7

<400> SEQUENCE: 9
agagatcgga agagcacacg tctgaactcc agtcacccgg aacgaaatct cgtatgccgt            60
cttctgcttg                                                                  70

<210> SEQ ID NO 10
<211> LENGTH: 75
<212> TYPE: DNA
<213> ORGANISM: Artificial
<220> FEATURE:
<223> OTHER INFORMATION: UDI_TC_index_D_A01_i5

<400> SEQUENCE: 10
aatgatacgg cgaccaccga gatctacacc tacactatga cactctttcc ctacacgacg            60
ctcttccgat ctctt                                                            75

<210> SEQ ID NO 11
<211> LENGTH: 70
<212> TYPE: DNA
<213> ORGANISM: Artificial
<220> FEATURE:
<223> OTHER INFORMATION: UDI_GC_index_D_A01_i7

```
<400> SEQUENCE: 11
cgagatcgga agagcacacg tctgaactcc agtcacccgg aacgaaatct cgtatgccgt    60
cttctgcttg                                                           70

<210> SEQ ID NO 12
<211> LENGTH: 75
<212> TYPE: DNA
<213> ORGANISM: Artificial
<220> FEATURE:
<223> OTHER INFORMATION: UDI_GC_index_D_A01_i5

<400> SEQUENCE: 12
aatgatacgg cgaccaccga gatctacacc tacactatga cactctttcc ctacacgacg    60
ctcttccgat ctcgt                                                     75

<210> SEQ ID NO 13
<211> LENGTH: 70
<212> TYPE: DNA
<213> ORGANISM: Artificial
<220> FEATURE:
<223> OTHER INFORMATION: UDI_AC_index_D_A01_i7

<400> SEQUENCE: 13
tgagatcgga agagcacacg tctgaactcc agtcacccgg aacgaaatct cgtatgccgt    60
cttctgcttg                                                           70

<210> SEQ ID NO 14
<211> LENGTH: 75
<212> TYPE: DNA
<213> ORGANISM: Artificial
<220> FEATURE:
<223> OTHER INFORMATION: UDI_AC_index_D_A01_i5

<400> SEQUENCE: 14
aatgatacgg cgaccaccga gatctacacc tacactatga cactctttcc ctacacgacg    60
ctcttccgat ctcat                                                     75

<210> SEQ ID NO 15
<211> LENGTH: 70
<212> TYPE: DNA
<213> ORGANISM: Artificial
<220> FEATURE:
<223> OTHER INFORMATION: UDI_CG_index_D_A01_i7

<400> SEQUENCE: 15
gcagatcgga agagcacacg tctgaactcc agtcacccgg aacgaaatct cgtatgccgt    60
cttctgcttg                                                           70

<210> SEQ ID NO 16
<211> LENGTH: 75
<212> TYPE: DNA
<213> ORGANISM: Artificial
<220> FEATURE:
<223> OTHER INFORMATION: UDI_CG_index_D_A01_i5

<400> SEQUENCE: 16
aatgatacgg cgaccaccga gatctacacc tacactatga cactctttcc ctacacgacg    60
ctcttccgat ctgct                                                     75

<210> SEQ ID NO 17
<211> LENGTH: 70
```

<212> TYPE: DNA
<213> ORGANISM: Artificial
<220> FEATURE:
<223> OTHER INFORMATION: UDI_TG_index_D_A01_i7

<400> SEQUENCE: 17
acagatcgga agagcacacg tctgaactcc agtcacccgg aacgaaatct cgtatgccgt    60
cttctgcttg                                                          70

<210> SEQ ID NO 18
<211> LENGTH: 75
<212> TYPE: DNA
<213> ORGANISM: Artificial
<220> FEATURE:
<223> OTHER INFORMATION: UDI_TG_index_D_A01_i5

<400> SEQUENCE: 18
aatgatacgg cgaccaccga gatctacacc tacactatga cactctttcc ctacacgacg    60
ctcttccgat ctgtt                                                    75

<210> SEQ ID NO 19
<211> LENGTH: 70
<212> TYPE: DNA
<213> ORGANISM: Artificial
<220> FEATURE:
<223> OTHER INFORMATION: UDI_GG_index_D_A01_i7

<400> SEQUENCE: 19
ccagatcgga agagcacacg tctgaactcc agtcacccgg aacgaaatct cgtatgccgt    60
cttctgcttg                                                          70

<210> SEQ ID NO 20
<211> LENGTH: 75
<212> TYPE: DNA
<213> ORGANISM: Artificial
<220> FEATURE:
<223> OTHER INFORMATION: UDI_GG_index_D_A01_i5

<400> SEQUENCE: 20
aatgatacgg cgaccaccga gatctacacc tacactatga cactctttcc ctacacgacg    60
ctcttccgat ctggt                                                    75

<210> SEQ ID NO 21
<211> LENGTH: 70
<212> TYPE: DNA
<213> ORGANISM: Artificial
<220> FEATURE:
<223> OTHER INFORMATION: UDI_AG_index_D_A01_i7

<400> SEQUENCE: 21
tcagatcgga agagcacacg tctgaactcc agtcacccgg aacgaaatct cgtatgccgt    60
cttctgcttg                                                          70

<210> SEQ ID NO 22
<211> LENGTH: 75
<212> TYPE: DNA
<213> ORGANISM: Artificial
<220> FEATURE:
<223> OTHER INFORMATION: UDI_AG_index_D_A01_i5

<400> SEQUENCE: 22
aatgatacgg cgaccaccga gatctacacc tacactatga cactctttcc ctacacgacg    60

```
ctcttccgat ctgat                                              75

<210> SEQ ID NO 23
<211> LENGTH: 58
<212> TYPE: DNA
<213> ORGANISM: Artificial
<220> FEATURE:
<223> OTHER INFORMATION: Adaptor-universal-UMI-i5

<400> SEQUENCE: 23
aatgatacgg cgaccaccga gatctacact ctttccctac acgacgctct tccgatct    58

<210> SEQ ID NO 24
<211> LENGTH: 65
<212> TYPE: DNA
<213> ORGANISM: Artificial
<220> FEATURE:
<223> OTHER INFORMATION: UMI_Index_1

<400> SEQUENCE: 24
gatcggaaga gcacacgtct gaactccagt cacatgccta atctcgtat gccgtcttct    60 gcttg                                                             65

<210> SEQ ID NO 25
<211> LENGTH: 65
<212> TYPE: DNA
<213> ORGANISM: Artificial
<220> FEATURE:
<223> OTHER INFORMATION: UMI_Index_2

<400> SEQUENCE: 25
gatcggaaga gcacacgtct gaactccagt cacgaatctg atctcgtat gccgtcttct    60 gcttg                                                             65

<210> SEQ ID NO 26
<211> LENGTH: 65
<212> TYPE: DNA
<213> ORGANISM: Artificial
<220> FEATURE:
<223> OTHER INFORMATION: UMI_Index_3

<400> SEQUENCE: 26
gatcggaaga gcacacgtct gaactccagt cacaacgtga tatctcgtat gccgtcttct    60
gcttg                                                             65

<210> SEQ ID NO 27
<211> LENGTH: 65
<212> TYPE: DNA
<213> ORGANISM: Artificial
<220> FEATURE:
<223> OTHER INFORMATION: UMI_Index_4

<400> SEQUENCE: 27
gatcggaaga gcacacgtct gaactccagt caccacttcg aatctcgtat gccgtcttct    60
gcttg                                                             65

<210> SEQ ID NO 28
<211> LENGTH: 65
<212> TYPE: DNA
<213> ORGANISM: Artificial
<220> FEATURE:
<223> OTHER INFORMATION: UMI_Index_5

<400> SEQUENCE: 28
```
gatcggaaga gcacacgtct gaactccagt cacgccaaga catctcgtat gccgtcttct    60
gcttg    65

<210> SEQ ID NO 29
<211> LENGTH: 65
<212> TYPE: DNA
<213> ORGANISM: Artificial
<220> FEATURE:
<223> OTHER INFORMATION: UMI_Index_6

<400> SEQUENCE: 29
gatcggaaga gcacacgtct gaactccagt cacgactagt aatctcgtat gccgtcttct    60
gcttg    65

<210> SEQ ID NO 30
<211> LENGTH: 65
<212> TYPE: DNA
<213> ORGANISM: Artificial
<220> FEATURE:
<223> OTHER INFORMATION: UMI_Index_7

<400> SEQUENCE: 30
gatcggaaga gcacacgtct gaactccagt cacattggct catctcgtat gccgtcttct    60
gcttg    65

<210> SEQ ID NO 31
<211> LENGTH: 65
<212> TYPE: DNA
<213> ORGANISM: Artificial
<220> FEATURE:
<223> OTHER INFORMATION: UMI_Index_8

<400> SEQUENCE: 31
gatcggaaga gcacacgtct gaactccagt cacgatgaat catctcgtat gccgtcttct    60
gcttg    65

<210> SEQ ID NO 32
<211> LENGTH: 65
<212> TYPE: DNA
<213> ORGANISM: Artificial
<220> FEATURE:
<223> OTHER INFORMATION: UMI_Index_9

<400> SEQUENCE: 32
gatcggaaga gcacacgtct gaactccagt cacagcagga aatctcgtat gccgtcttct    60
gcttg    65

<210> SEQ ID NO 33
<211> LENGTH: 65
<212> TYPE: DNA
<213> ORGANISM: Artificial
<220> FEATURE:
<223> OTHER INFORMATION: UMI_Index_10

<400> SEQUENCE: 33
gatcggaaga gcacacgtct gaactccagt cacgagctga aatctcgtat gccgtcttct    60
gcttg    65

<210> SEQ ID NO 34
<211> LENGTH: 65
<212> TYPE: DNA

```
<213> ORGANISM: Artificial
<220> FEATURE:
<223> OTHER INFORMATION: UMI_Index_11

<400> SEQUENCE: 34
gatcggaaga gcacacgtct gaactccagt cacaaacatc gatctcgtat gccgtcttct      60
gcttg                                                                 65

<210> SEQ ID NO 35
<211> LENGTH: 65
<212> TYPE: DNA
<213> ORGANISM: Artificial
<220> FEATURE:
<223> OTHER INFORMATION: UMI_Index_12

<400> SEQUENCE: 35
gatcggaaga gcacacgtct gaactccagt cacgagttag catctcgtat gccgtcttct      60
gcttg                                                                 65

<210> SEQ ID NO 36
<211> LENGTH: 65
<212> TYPE: DNA
<213> ORGANISM: Artificial
<220> FEATURE:
<223> OTHER INFORMATION: UMI_Index_13

<400> SEQUENCE: 36
gatcggaaga gcacacgtct gaactccagt caccgaactt aatctcgtat gccgtcttct      60
gcttg                                                                 65

<210> SEQ ID NO 37
<211> LENGTH: 65
<212> TYPE: DNA
<213> ORGANISM: Artificial
<220> FEATURE:
<223> OTHER INFORMATION: UMI_Index_14

<400> SEQUENCE: 37
gatcggaaga gcacacgtct gaactccagt cacgatagac aatctcgtat gccgtcttct      60
gcttg                                                                 65

<210> SEQ ID NO 38
<211> LENGTH: 65
<212> TYPE: DNA
<213> ORGANISM: Artificial
<220> FEATURE:
<223> OTHER INFORMATION: UMI_Index_15

<400> SEQUENCE: 38
gatcggaaga gcacacgtct gaactccagt cacaaggaca catctcgtat gccgtcttct      60
gcttg                                                                 65

<210> SEQ ID NO 39
<211> LENGTH: 65
<212> TYPE: DNA
<213> ORGANISM: Artificial
<220> FEATURE:
<223> OTHER INFORMATION: UMI_Index_16

<400> SEQUENCE: 39
gatcggaaga gcacacgtct gaactccagt cacgacagtg catctcgtat gccgtcttct      60
gcttg                                                                 65
```

<210> SEQ ID NO 40
<211> LENGTH: 65
<212> TYPE: DNA
<213> ORGANISM: Artificial
<220> FEATURE:
<223> OTHER INFORMATION: UMI_Index_17

<400> SEQUENCE: 40
gatcggaaga gcacacgtct gaactccagt cacatcattc catctcgtat gccgtcttct    60
gcttg    65

<210> SEQ ID NO 41
<211> LENGTH: 65
<212> TYPE: DNA
<213> ORGANISM: Artificial
<220> FEATURE:
<223> OTHER INFORMATION: UMI_Index_18

<400> SEQUENCE: 41
gatcggaaga gcacacgtct gaactccagt cacgccacat aatctcgtat gccgtcttct    60
gcttg    65

<210> SEQ ID NO 42
<211> LENGTH: 65
<212> TYPE: DNA
<213> ORGANISM: Artificial
<220> FEATURE:
<223> OTHER INFORMATION: UMI_Index_19

<400> SEQUENCE: 42
gatcggaaga gcacacgtct gaactccagt cacaccactg tatctcgtat gccgtcttct    60
gcttg    65

<210> SEQ ID NO 43
<211> LENGTH: 65
<212> TYPE: DNA
<213> ORGANISM: Artificial
<220> FEATURE:
<223> OTHER INFORMATION: UMI_Index_20

<400> SEQUENCE: 43
gatcggaaga gcacacgtct gaactccagt cacctggcat aatctcgtat gccgtcttct    60
gcttg    65

<210> SEQ ID NO 44
<211> LENGTH: 65
<212> TYPE: DNA
<213> ORGANISM: Artificial
<220> FEATURE:
<223> OTHER INFORMATION: UMI_Index_21

<400> SEQUENCE: 44
gatcggaaga gcacacgtct gaactccagt cacacctcca atctcgtat gccgtcttct    60 gcttg    65

<210> SEQ ID NO 45
<211> LENGTH: 65
<212> TYPE: DNA
<213> ORGANISM: Artificial
<220> FEATURE:
<223> OTHER INFORMATION: UMI_Index_22

<400> SEQUENCE: 45
gatcggaaga gcacacgtct gaactccagt cacgcgagta aatctcgtat gccgtcttct    60
gcttg                                                                65

<210> SEQ ID NO 46
<211> LENGTH: 65
<212> TYPE: DNA
<213> ORGANISM: Artificial
<220> FEATURE:
<223> OTHER INFORMATION: UMI_Index_23

<400> SEQUENCE: 46
gatcggaaga gcacacgtct gaactccagt cacactatgc aatctcgtat gccgtcttct    60
gcttg                                                                65

<210> SEQ ID NO 47
<211> LENGTH: 65
<212> TYPE: DNA
<213> ORGANISM: Artificial
<220> FEATURE:
<223> OTHER INFORMATION: UMI_Index_24

<400> SEQUENCE: 47
gatcggaaga gcacacgtct gaactccagt caccggattg catctcgtat gccgtcttct    60
gcttg                                                                65

<210> SEQ ID NO 48
<211> LENGTH: 65
<212> TYPE: DNA
<213> ORGANISM: Artificial
<220> FEATURE:
<223> OTHER INFORMATION: UMI_Index_25

<400> SEQUENCE: 48
gatcggaaga gcacacgtct gaactccagt cacaactcac catctcgtat gccgtcttct    60
gcttg                                                                65

<210> SEQ ID NO 49
<211> LENGTH: 65
<212> TYPE: DNA
<213> ORGANISM: Artificial
<220> FEATURE:
<223> OTHER INFORMATION: UMI_Index_26

<400> SEQUENCE: 49
gatcggaaga gcacacgtct gaactccagt cacgctaacg aatctcgtat gccgtcttct    60
gcttg                                                                65

<210> SEQ ID NO 50
<211> LENGTH: 65
<212> TYPE: DNA
<213> ORGANISM: Artificial
<220> FEATURE:
<223> OTHER INFORMATION: UMI_Index_27

<400> SEQUENCE: 50
gatcggaaga gcacacgtct gaactccagt caccagatct gatctcgtat gccgtcttct    60
gcttg                                                                65

<210> SEQ ID NO 51
<211> LENGTH: 65

```
<212> TYPE: DNA
<213> ORGANISM: Artificial
<220> FEATURE:
<223> OTHER INFORMATION: UMI_Index_28

<400> SEQUENCE: 51
gatcggaaga gcacacgtct gaactccagt cacatcctgt aatctcgtat gccgtcttct    60
gcttg                                                                65

<210> SEQ ID NO 52
<211> LENGTH: 65
<212> TYPE: DNA
<213> ORGANISM: Artificial
<220> FEATURE:
<223> OTHER INFORMATION: UMI_Index_29

<400> SEQUENCE: 52
gatcggaaga gcacacgtct gaactccagt cacctgtagc catctcgtat gccgtcttct    60
gcttg                                                                65

<210> SEQ ID NO 53
<211> LENGTH: 65
<212> TYPE: DNA
<213> ORGANISM: Artificial
<220> FEATURE:
<223> OTHER INFORMATION: UMI_Index_30

<400> SEQUENCE: 53
gatcggaaga gcacacgtct gaactccagt cacgctcggt aatctcgtat gccgtcttct    60
gcttg                                                                65

<210> SEQ ID NO 54
<211> LENGTH: 65
<212> TYPE: DNA
<213> ORGANISM: Artificial
<220> FEATURE:
<223> OTHER INFORMATION: UMI_Index_31

<400> SEQUENCE: 54
gatcggaaga gcacacgtct gaactccagt cacacacgac catctcgtat gccgtcttct    60
gcttg                                                                65

<210> SEQ ID NO 55
<211> LENGTH: 65
<212> TYPE: DNA
<213> ORGANISM: Artificial
<220> FEATURE:
<223> OTHER INFORMATION: UMI_Index_32

<400> SEQUENCE: 55
gatcggaaga gcacacgtct gaactccagt cacagtcact aatctcgtat gccgtcttct    60
gcttg                                                                65
```